(12) United States Patent
Bosch et al.

(10) Patent No.: US 8,293,899 B2
(45) Date of Patent: Oct. 23, 2012

(54) PROCESS FOR REDUCING 3-HETEROARYL-3-OXOPROPIONIC ACID DERIVATIVES

(75) Inventors: Boris Bosch, Köln (DE); Markus Eckert, Shanghai (CN); Hans-Christian Militzer, Odenthal (DE); Claus Dreisbach, Leichlingen (DE)

(73) Assignee: Lanxess Deutschland GmbH, Leverkusen (DE)

( * ) Notice: Subject to any disclaimer, the term of this patent is extended or adjusted under 35 U.S.C. 154(b) by 0 days.

(21) Appl. No.: 10/375,344

(22) Filed: Feb. 27, 2003

(65) Prior Publication Data

US 2003/0225274 A1    Dec. 4, 2003

(30) Foreign Application Priority Data

Mar. 1, 2002   (DE) ................. 102 08 828

(51) Int. Cl.
| | |
|---|---|
| *C07D 333/36* | (2006.01) |
| *C07D 221/06* | (2006.01) |
| *C07D 277/56* | (2006.01) |
| *C07D 475/02* | (2006.01) |
| *C07D 233/44* | (2006.01) |

(52) U.S. Cl. ........ 544/224; 544/257; 544/335; 544/406; 546/110; 546/341; 548/201; 548/332.1; 548/360.1; 548/368.4; 548/572; 549/69

(58) Field of Classification Search .................. 546/341; 549/58, 79, 499, 74, 75, 76, 77, 78
See application file for complete search history.

(56) References Cited

U.S. PATENT DOCUMENTS

| | | | | |
|---|---|---|---|---|
| 6,380,257 | B1 * | 4/2002 | Vertesy et al. | 514/569 |
| 6,437,140 | B1 * | 8/2002 | Kim et al. | 546/341 |
| 6,610,878 | B1 * | 8/2003 | Hubbs et al. | 560/124 |
| 6,921,822 | B2 * | 7/2005 | Militzer et al. | 540/450 |
| 2005/0107621 | A1 | 5/2005 | Takehara et al. | |

OTHER PUBLICATIONS

Madec, J. et al, "Asymmetric hydrogenation reactions using practical in situ generation of chiral ruthenium-diphosphine catalysts from anhydrous RuCl3", Chem. Abs.135:60899, 2001.*
Miller, Robert E., "Thiophene series. VII. The application of the Reformatskii reaction to thiophene aldehydes and ketones", Chem. Abs.44:22544, 1950.*
Runti, C. et al, "New Nitriles and Amides of Aromatic and Heterocyclic Ketones", Chem.Abs.55:54340, 1961.*
Genet et al., Tetrahedron Letters, vol. 36, pp. 4801-4804, 1995.*
Tetrahedron Asymmetry 10, (month unavailable) 1999, pp. 2045-2061, Matthew J. Palmer and Martin Wills, Aysmmetric transfer hydrogenation of C=O= and C=N bonds.
JACS, 118, (month unavailable) 1996, pp. 251-2522, Akio Fujii et al, "Ruthenium (II)-Catalyzed Asymmetric Transfer Hydrogenation of Ketones Using a Formic Acid-Triethylamine Mixture".
Acc. Chem. Res., 30 (month unavailable) 1997, pp. 97-102, Ryoji Noyori et al, "Asymmetric.Transfer Hydrogenation Catalyzed by Chiral Ruthenium Complexes".
Chem. Rev., 92, (month unavailable) 1992, pp. 1051-1069, Grazia Zassinovich et al, "Asymmetric Hydrogen Transfer Reactions Promoted by Homogeneous Transition Metal Catalysts".

* cited by examiner

*Primary Examiner* — Sun Jae Loewe
(74) *Attorney, Agent, or Firm* — Norris McLaughlin & Marcus, P.A.

(57) ABSTRACT

The present invention relates to a process for preparing stereoisomerically enriched 3-heteroaryl-3-hydroxycarboxylic esters by reducing 3-heteroaryl-3-oxocarboxylic esters in the presence of ruthenium-containing catalysts.

18 Claims, No Drawings

PROCESS FOR REDUCING 3-HETEROARYL-3-OXOPROPIONIC ACID DERIVATIVES

BACKGROUND OF THE INVENTION

The present invention relates to a process for preparing stereoisomerically enriched 3-heteroaryl-3-hydroxypropionic acid derivatives by reducing 3-heteroaryl-3-oxopropionic acid derivatives in the presence of ruthenium-containing catalysts.

Stereoisomerically enriched 3-hydroxypropionic acid derivatives, in particular those which bear a heteroaryl radical in the 3-position, are valuable intermediates, for example, in the preparation of liquid-crystalline compounds, agrochemicals and pharmaceuticals.

Process for preparation comprising the catalytic reduction of ketones to stereoisomerically enriched secondary alcohols is known in principle. Useful reducing agents are typically molecular hydrogen or, in the case of transfer hydrogenations, organic hydrogen donors, for example formic acid or isopropanol. An advantage of transfer hydrogenations is that the safety precautions which have to be taken when handling highly flammable molecular hydrogen under pressure can be dispensed with. It is also generally possible to work at ambient pressure. A review of transfer hydrogenations as a method for catalytic reduction of ketones is given, for example, by Zassinovich et al. in Chem. Rev. 1992, 92, 1051-1069 and Noyori et al. in Ace. Chem. Res. 1997, 30, 97-102 and Wills et al. in Tetrahedron, Asymmetry, 1999, 2045.

Noyori et al. (JACS 1996, 118, 2521-2522, Ace. Chem. Res. 1997, 30, 97-102) describe the use of ruthenium complexes as catalysts and triethylamine/formic acid for the enantioselective reduction of simple ketones.

However, there still existed the need to provide an efficient process which allows the preparation of stereoisomerically enriched 3-heteroaryl-3-hydroxypropionic acid derivatives from 3-heteroaryl-3-oxopropionic acid derivatives.

SUMMARY OF THE INVENTION

A process has now been found for preparing stereoisomerically enriched 3-hetero-aryl-3-hydroxypropionic acid derivatives, which is characterized in that
a) compounds of the formula (I)

heteroaryl-CO—CH$_2$W    (I);

where
heteroaryl is a mono-, bi- or tricyclic aromatic radical having a total of from 5 to 18 ring atoms where each cycle may have no, one, two or three ring atoms and there may be one, two, three, four or five ring atoms in the entire aromatic radical selected from the group of oxygen, sulphur and nitrogen, and where the mono-, bi- or tricyclic aromatic radical may optionally be mono- or polysubstituted and
W is C(O)YR$^1{}_n$, where Y is oxygen and n=1 or Y is nitrogen and n=2, or
W is CN, and
R$^1$ is in each case independently hydrogen, C$_1$-C$_{20}$-alkyl, C$_4$-C$_{14}$-aryl or C$_5$-C$_{15}$-arylalkyl or, in the case that Y is nitrogen, both R$^1$ radicals together are C$_3$-C$_{12}$-alkylene,
b) in the presence of a ruthenium-containing catalyst and
c) in the presence of at least one amine, at least some of which is present in protonated form,
d) are reacted with formic acid, formates or mixtures thereof
e) optionally in the presence of organic solvent.

As would be realized, the scope of the invention also encompasses any desired combinations of the ranges and preferred ranges specified for each feature.

DETAILED DESCRIPTION OF THE INVENTION

The invention is described more fully herunder with particular reference to specific embodiments thereof. For the purposes of the invention, stereoisomerically enriched (enantiomerically enriched, diastereomerically enriched) 3-heteroaryl-3-hydroxypropionic acid derivatives are stereoisomerically pure (enantiomerically pure or diastereomerically pure) 3-heteroaryl-3-hydroxy-propionic acid derivatives or mixtures of stereoisomeric (enantiomeric or diastereomeric) 3-heteroaryl-3-hydroxypropionic acid derivatives in which one stereoisomer (enantiomer or diastereomer) is present in a larger absolute portion, preferably 70 to 100 mol % and very particularly preferably 85 to 100 mol %, than another diastereomer, or than the other enantiomer.

For the purposes of the invention, alkyl is, in each case independently, a straight-chain or cyclic, and, independently thereof, branched or unbranched, alkyl radical which may be further substituted by C$_1$-C$_4$-alkoxy radicals. The same applies for the alkylene moiety of an arylalkyl radical -;

For the purposes of the invention, alkyl can be C$_1$-C$_4$-alkyl, for example, methyl, ethyl, 2-ethoxyethyl, n-propyl, isopropyl, n-butyl and tert-butyl; C$_1$-C$_8$-alkyl, for example, n-pentyl, cyclohexyl, n-hexyl, n-heptyl, n-octyl or isooctyl; C$_1$-C$_{12}$-alkyl, for example, norbornyl, n-decyl and n-dodecyl, and C$_1$-C$_{20}$, for example, n-hexadecyl and n-octadecyl.

For the purposes of the invention, aryl is, for example and with preference, carbocyclic aromatic radicals or heteroaromatic radicals which contain no, one, two or three heteroatoms per cycle, but at least one heteroatom in the entire heteroaromatic radical which is selected from the group of nitrogen, sulphur and oxygen.

The carbocyclic aromatic radicals or heteroaromatic radicals may further be substituted by up to five substituents per cycle, each of which is, for example and with preference, independently selected from the group of hydroxyl, C$_1$-C$_{12}$-alkyl, cyano, COOH, COOM where M is an alkali metal ion or half an equivalent of an alkaline earth metal ion, COO—(C$_1$-C$_{12}$-alkyl), COO—(C$_4$-C$_{10}$-aryl), CO—(C$_1$-C$_{12}$-alkyl), CO—(C$_4$-C$_{10}$-aryl), O—(C$_1$-C$_{12}$-alkyl), O—(C$_4$-C-10-aryl), N(C$_1$-C$_{12}$-alkyl)$_2$, NH—(C$_1$-C$_{12}$-alkyl), fluorine, chlorine, bromine, C$_1$-C$_{12}$-fluoroalkyl where fluoroalkyl is a singly, multiply or fully fluorine-substituted alkyl radical as defined above, CONH$_2$, CONH—(C$_1$-C$_{12}$-alkyl), NHCOO—(C$_1$-C$_{12}$-alkyl). The same applies to the aryl moiety of an arylalkyl radical.

In formula (I), heteroaryl is preferably a mono- or bicyclic aromatic radical having a total of 5 to 12 ring atoms where, in each cycle, no, one or two, and in the entire aromatic radical, one, two, three or four, ring atoms selected from the group of oxygen, sulphur and nitrogen may be present, and where the mono- or bicyclic aromatic radical bears no, one, two or three radicals per cycle which are each independently selected from the group of hydroxyl, C$_1$-C$_{12}$-alkyl, cyano, COOH, COOM, COO—(C$_1$-C$_{12}$-alkyl), COO—(C$_4$-C$_{10}$-aryl), CO—(C$_1$-C$_{12}$-alkyl), CO—(C$_4$-C$_{10}$-aryl), O—(C$_1$-C$_{12}$-alkyl), (C$_1$-C$_{12}$-alkyl)-O—(C$_1$-C$_{12}$alkyl), (C$_4$-C$_{10}$aryl)-O—(C$_1$-C$_{12}$-alkyl), O—(C$_4$-C$_{10}$-aryl), O—CO—(C$_4$-C$_{10}$-aryl), O—CO—(C$_1$-C$_{12}$-alkyl), OCOO—(C$_1$-C$_{12}$-alkyl), N—(C$_1$-C$_{12}$-alkyl)$_2$, NH—(C$_1$C$_{12}$-alkyl), N(C$_4$-C$_{10}$-aryl)$_2$, NH—(C$_4$-C$_{10}$-aryl), fluorine, chlorine, bromine, iodine, NO$_2$, SO$_3$H, SO$_3$M, SO$_2$(C$_1$-C$_{12}$-alkyl), SO(C$_1$-C$_{12}$-alkyl), C$_1$-C$_{12}$-fluoroalkyl where fluoroalkyl is a singly, multiply or fully fluorine-substituted alkyl radical as defined above, NHCO—($C_1$-$C_{12}$-alkyl), $CONH_2$, CONH—($C_1$-$C_{12}$-alkyl), NHCOO—($C_1$-$C_{12}$-alkyl), PO($C_4$-$C_{10}$-aryl)$_2$, PO($C_1$-$C_{12}$-alkyl)$_2$, $PO_3H_2$, $PO_3M_2$, $PO_3HM$, PO(O($C_1$-$C_{12}$-alkyl)$_2$, where M is in each case an alkali metal ion or half an equivalent of an alkaline earth metal ion.

In formula (I), heteroaryl is particularly preferably 2- or 3-thiophenyl, 2- or 3-furanyl, 2- or 3-pyrrolyl, 3- or 4-pyrazolyl 1-, 2-; or 4-thiazolyl, 1-, 2-, or 4oxazolyl, 2-, 4- or 5-imidazolyl, 2-, 3-, or 4-pyridyl, 2- or 3-pyrazinyl, 2-, 4-, or 5-pyrimidyl, 3-, 4-, 5- or 6-pyridazinyl, 2- or 3-indolyl, 3-indazolyl, indazolyl, 2- or 3-benzofuranyl, 2- or 3-benzothiophen-yl, 2-, 3- or 4-quinolinyl, isoquinolinyl 2-, 4-, 6- or 7-pteridinyl or 2-, 3-, 4-, 5-, 6-, 8-, 9- or 10-phenanthrenyl where each of the radicals mentioned bears no, one or two radicals per cycle, each of which is independently selected from the group of $C_1$-$C_4$-alkyl, cyano, COO—($C_1$-$C_4$-alkyl), O—($C_1$-$C_4$-alkyl), N($C_1$-$C_4$-alkyl)$_2$, NH—($C_1$-$C_4$-alkyl), fluorine, chlorine, bromine or $C_1$-$C_4$-fluoroalkyl, for example trifluoromethyl, 2,2,2-trifluoroethyl or pentafluoroethyl.

Heteroaryl in formula (I) is very particularly preferably 2-thiophen-yl.

W in formula (I) is preferably COOR$^1$ where R$^1$ is hydrogen the $C_1$-$C_8$-alkyl.

R$^1$ in formula (I) is preferably $C_1$-$C_{12}$-alkyl, phenyl, o-, m- or p-tolyl, p-nitro-phenyl or benzyl.

R$^1$ in formula (I) is particularly preferably methyl, ethyl, 2-ethoxyethyl, n-propyl, isopropyl, n-butyl, tert-butyl, n-pentyl, cyclohexyl and n-hexyl, and also trifluoro-methyl, chloromethyl, benzyl and phenyl, and also 1,5-pentylene, 1,4-butylene and 3-propylene.

Very particularly preferred compounds of the formula (I) are methyl 3-oxo-3-(4-pyridinyl)propanoate, ethyl 3-oxo-3-(4-pyridinyl)propanoate, isopropyl 3-oxo-3-(4-pyridinyl)propanoate, tert-butyl 3-oxo-3-(4-pyridinyl)propanoate, 2-ethyl-hexyl 3-oxo-3-(4-pyridinyl)propanoate, 3-oxo-3-(4-pyridinyl)propanamide, N,N-dimethyl-3-oxo-3-(4-pyridinyl)propanamide, N-methyl-3-oxo-3-(4-pyridinyl) propanamide, N,N-diethyl-3-oxo-3-(4-pyridinyl)propanamide,N-ethyl-3-oxo-3-(4-pyridinyl) propanamide, 3-oxo-3-(N-piperidinyl)-1-(4-pyridinyl)- 1 -propanone, 3-oxo-3-(N-pyrrolidinyl)-1-(4-pyridinyl)-1-propanone, 3-oxo-3-(4-pyridinyl) propanenitrile, methyl 3-oxo-3-(3-pyridinyl)propanoate, ethyl 3-oxo-3-(3-pyridinyl)propanoate, isopropyl 3-oxo-3-(3-pyridinyl)propanoate, tert-butyl 3-oxo-3-(3-pyridinyl)propanoate, 2-ethylhexyl 3-oxo-3-(3-pyridinyl)propanoate, 3-oxo-3-(3-pyridinyl)propanamide, N,N-dimethyl-3-oxo-3-(3-pyridinyl)propanamide, N-methyl-3-oxo-3-(3-pyridinyl)propanamide, N,N-diethyl-3-oxo-3-(3-pyridinyl)propanamide, N-ethyl-3-oxo-3-(3-pyridinyl) propanamide, 3-oxo-3-(N-piperidinyl)-1-(3-pyridinyl)-1-propanone, 3-oxo-3-(N-pyrrolidinyl)-1-(3-pyridinyl)-1-propanone, 3-oxo-3-(3-pyridinyl)propanenitrile, methyl 3-oxo-3-(2-pyridinyl)propanoate, ethyl 3-oxo-3-(2-pyridinyl)propanoate, isopropyl 3-oxo-3-(2-pyridinyl)propanoate, tert-butyl 3-oxo-3-(2-pyridinyl)propanoate, 2-ethylhexyl 3-oxo-3-(2-pyridinyl)propanoate, 3-oxo-3-(2-pyridinyl)propanamide, N,N-dimethyl-3-oxo-3-(2-pyridinyl)propanamide, N-methyl-3-oxo-3-(2-pyridinyl)propanamide, N,N-diethyl-3-oxo-3-(2-pyridinyl)propanamide, N-ethyl-3-oxo-3-(2-pyridinyl)propanamide, 3-oxo-3-(N-piperidinyl)-1-(2-pyridinyl)-1-propanone, 3-oxo-3-(N-pyrrolidinyl)-1-(2-pyridinyl)-1-propanone, 3-oxo-3-(2-pyridinyl) propanenitrile, methyl 3-oxo-3-(5-pyrimidinyl)propanoate, ethyl 3-oxo-3-(5-pyrimidinyl)propanoate, isopropyl 3-oxo-3-(5-pyrimidinyl)propanoate, tert-butyl 3-oxo-3-(5-pyrimidinyl)propanoate, 2-ethylhexyl 3-oxo-3-(5-pyrimidinyl) propanoate, 3-oxo-3-(5-pyrimidinyl)propanamide, N,N-dimethyl-3-oxo-3-(5-pyrimidinyl)-propanamide, N-methyl-3-oxo-3-(5-pyrimidinyl) propanamide, N,N-diethyl-3-oxo-3-(5-pyrimidinyl)propanamide, N-ethyl-3-oxo-3-(5-pyrimidinyl)propanamide, 3-oxo-3-(N-piperidinyl)-1-(5-pyrimidinyl)-1-propanone, 3-oxo-3-(N-pyrrolidinyl)-1-(5-pyrimidinyl)-1-propanone, 3-oxo-3-(5-pyrimidinyl) propanenitrile, methyl 3-oxo-3-(4-pyrimidinyl)propanoate, ethyl 3-oxo-3-(4-pyrimidinyl)propanoate, isopropyl 3-oxo-3-(4-pyrimidinyl)propanoate, tert-butyl 3-oxo-3-(4-pyrimidinyl)propanoate, 2-ethylhexyl 3-oxo-3-(4-pyrimidinyl) propanoate, 3-oxo-3-(4-pyrimidinyl)propanamide, N,N-dimethyl-3-oxo-3-(4-pyrimidinyl)propanamide, N-methyl-3-oxo-3-(4-pyrimidinyl)propanamide, N,N-diethyl-3-oxo-3-(4-pyrimidinyl)propanamide, N-ethyl-3-oxo-3-(4-pyrimidinyl)propanamide, 3-oxo-3-(N-piperidinyl)-1-(4-pyrimidinyl)-1-propanone, 3-oxo-3-(N-pyrrolidinyl)-1-(4-pyrimidinyl)-1-propanone, 3-oxo-3-(4-pyrimidinyl) propanenitrile, methyl 3-oxo-3-(2-pyrimidinyl)propanoate, ethyl 3-oxo-3-(2-pyrimidinyl)propanoate, isopropyl 3-oxo-3-(2-pyrimidinyl) propanoate, tert-butyl 3-oxo-3-(2-pyrimidinyl)propanoate, 2-ethylhexyl 3-oxo-3-(2-pyrimidinyl) propanoate, 3-oxo-3-(2-pyrimidinyl)propanamide, N,N-dimethyl-3-oxo-3-(2-pyrimidinyl)propanamide, N-methyl-3-oxo-3-(2-pyrimidinyl)-propanamide, N,N-diethyl-3-oxo-3-(2-pyrimidinyl)propanamide, N-ethyl-3-oxo-3-(2-pyrimidinyl)propanamide, 3-oxo-3-(N-piperidinyl)-1-(2-pyrimidinyl)-1-propanone, 3-oxo-3-(N-pyrrolidinyl)-1-(2-pyrimidinyl)-1-propanone, 3-oxo-3-(2-pyrimidinyl) propanenitrile, ethyl 3-(6-chloro-3-pyridinyl)-3-oxopropanoate, ethyl 3-(2,6-dichloro-3-pyridinyl)-3-oxopropanoate, ethyl 3-oxo-3-(4,5,6-trichloro-3-pyridinyl) propanoate, ethyl 3-(2,6-dichloro-5-fluoro-3-pyridinyl)-3-oxo-propanoate, methyl 3-(3-chloro-1-benzothien-2-yl)-3-oxopropanoate, methyl 3-oxo-3-(3-thiophenyl)propanoate, ethyl 3-oxo-3-(3-thiophenyl)propanoate, isopropyl 3-oxo-3-(3-thiophenyl)propanoate, tert-butyl 3-oxo-3-(3-thiophenyl) propanoate, 2-ethylhexyl 3-oxo-3-(3-thiophenyl)propanoate, 3-oxo-3-(3-thiophenyl)propanamide, N,N-dimethyl-3-oxo-3-(3-thiophenyl)propanamide, N-methyl-3-oxo-3-(3-thiophenyl)propanamide, N,N-diethyl-3-oxo-3-(3-thiophenyl)propanamide, N-ethyl-3-oxo-3-(3 thiophenyl) propanamide, 3-oxo-3-(N-piperidinyl)-1-(3-thiophenyl)-1-propanone, 3-3oxo-3-(N-pyrrolidinyl)-1-(3-thiophenyl)-1-propanone, 3-oxo-3-(3-thiophenyl)propanenitrile, methyl 3-oxo-3-(2-thiophenyl)propanoate, ethyl 3-oxo-3-(2-thiophenyl)propanoate, isopropyl 3-oxo-3-(2-thiophenyl) propanoate, tert-butyl 3-oxo-3-(2-thiophenyl)propanoate, 2-ethylhexyl 3-oxo-3-(2-thiophenyl)propanoate, 3-oxo-3-(2-thiophenyl) propanamide, N,N-dimethyl-3-oxo-3-(2-thiophenyl)propanamide, N,N-diethyl-3-oxo-3-(2-thiophenyl)propanamide, N-ethyl-3-oxo-3-(2-thiophenyl) propanamide, 3-oxo-3-(N-piperidinyl)-1-(2-thiophenyl)-1-propanone, 3-oxo-3-(N-pyrrolidinyl)-1-(2-thiophenyl)-1-propanone, 3-oxo-3-(2-thiophenyl)propanenitrile, methyl 3-oxo-3-(3-pyrrolyl)propanoate, ethyl 3-oxo-3-(3-pyrrolyl) propanoate, isopropyl 3-oxo-3-(3-pyrrolyl)propanoate, tert-butyl 3oxo-3-(3-pyrrolyl)propanoate, 2-ethylhexyl 3-oxo-3-(3-pyrrolyl)propanoate, 3-oxo0-3-(3-pyrrolyl)propanamide, N,N-dimethyl-3-oxo-3-(3-pyrrolyl)propanamide, N-methyl-3-oxo-3-(3-pyrrolyl)propanamide, N,N-diethyl-3-oxo-3-(3-pyrrolyl)propanamide, N-ethyl-3-oxo-3-(3-pyrrolyl)propanamide, 3-oxo-3-(N-piperidinyl)-1-(3-pyrrolyl)-1-propanone, 3-oxo-3-(N-pyrrolidinyl)-1-(3-pyrrolyl)-1-propanone, 3-oxo-3-(3-pyrrolyl)propanenitrile, methyl 3-oxo-3-(2-pyrrolyl)propanoate, ethyl 3-oxo-3-(2-pyrrolyl) propanoate, isopropyl 3-oxo-3-(2-pyrrolyl)propanoate, tert-butyl 3-oxo-3-(2-pyrrolyl)propanoate, 2-ethylhexyl 3-oxo-3-(2-pyrrolyl)propanoate, 3-oxo-3-(2-pyrrolyl)propanamide, N,N-dimethyl-3-oxo-3-(2-pyrrolyl)propanamide, N-methyl-3-oxo-3-(2-pyrrolyl)propanamide, N,N-diethyl-3-oxo-3-(2-pyrrolyl)propanamide, N-ethyl-3-oxo-3-(2-pyrrolyl)propanamide, 3-oxo-3-(N-piperidinyl)-1-(2-pyrrolyl)-1-propanone, 3-oxo-3-(N-pyrrolidinyl)-1-(2-pyrrolyl)-1-propanone, 3-oxo-3-(2-pyrrolyl)propanenitrile, methyl 3-oxo-3-(1-thiazolyl)propanoate, ethyl 3-oxo-3-(1-thiazolyl)propanoate, isopropyl 3-oxo-3-(1-thiazolyl)propanoate, tert-butyl 3-oxo-3-(1-thiazolyl)propanoate, 2-ethylhexyl 3-oxo-3-(1-thiazolyl)propanoate, 3-oxo-3-(1-thiazolyl)propanamide, N,N-dimethyl-3-oxo-3-(1-thiazolyl)propanamide, N-methyl-3-oxo-3-(1-thiazolyl)propanamide, N,N-diethyl-3-oxo-3-(1-thiazolyl) propanamide, N-ethyl-3-oxo-3-(1-thiazolyl)propanamide, 3-oxo-3-(N-piperidinyl)-1-(1-thiazolyl)-1-propanone, 3-oxo-3-(N-pyrrolidinyl)-1-(1-thiazolyl)-1-propanone, 3-oxo-3-(1-thiazolyl)propanenitrile, methyl 3-oxo-3-(2-thiazolyl) propanoate, ethyl 3-oxo-3-(1-thiazolyl)propanoate, isopropyl 3-oxo-3-(1-thiazolyl)propanoate, tert-butyl 3-oxo-3-(1-thiazolyl)propanoate, 2-ethylhexyl 3-oxo-3-(1-thiazolyl)propanoate, 3-oxo-3-(1-thiazolyl)propanamide, N,N-dimethyl-3-oxo-3-(1-thiazolyl)propanamide, N-methyl-3-oxo-3-(1-thiazolyl)propanamide, N,N-diethyl-3-oxo-3-(1-thiazolyl)propanamide, N-ethyl-3-oxo-3-(1-thiazolyl) propanamide, 3-oxo-3-(N-piperidinyl)-1-(1-thiazolyl)-1-propanone, 3-oxo-3-(N-pyrrolidinyl)-1-(1-thiazolyl)-1-propanone, 3-oxo-3-(1-thiazolyl)propanenitrile, methyl 3-oxo-3-(4-thiazolyl)propanoate, ethyl 3-oxo-3-(1-thiazolyl)propanoate, isopropyl 3-oxo-3-(1-thiazolyl)propanoate, tert-butyl 3-oxo-3-(1-thiazolyl)propanoate, 2-ethylhexyl 3-oxo-3-(1-thiazolyl)propanoate, 3-oxo-3-(1-thiazolyl)propanamide, N,N-dimethyl-3-oxo-3-(1-thiazolyl)propanamide, N-methyl-3-oxo-3-(1-thiazolyl)propanamide, N,N-diethyl-3-oxo-3-(1-thiazolyl)-propanamide, N-ethyl-3-oxo-3-( 1-thiazolyl)propanamide, 3-oxo-3-(N-piperidinyl)-1-(1-thiazolyl)-1-propanone, 3-oxo-3-(N-pyrrolidinyl)-1-(1-thiazolyl)-1-propanone, 3-oxo-3-( 1-thiazolyl)propanenitrile, methyl 3-oxo-3-( 1-oxazolyl) propanoate, ethyl 3-oxo-3-(1-thiazolyl)propanoate, isopropyl 3-oxo-3-(1-thiazolyl)propanoate, tert-butyl 3-oxo-3-(1-thiazolyl)propanoate, 2-ethylhexyl 3-oxo-3-(1-thiazolyl)propanoate, 3-oxo-3-(1-thiazolyl)propanamide, N,N-dimethyl-3-oxo-3-(1-thiazolyl)propanamide, N-methyl-3-oxo-3-(1-thiazolyl)propanamide, N,N-diethyl-3-oxo-3-(1-thiazolyl) propanamide, N-ethyl-3-oxo-3-(1-thiazolyl)propanamide, 3-oxo-3-(N-piperidinyl)-1-(1-thiazolyl)-1-propanone, 3-oxo-3-(N-pyrrolidinyl)-1-(1-thiazolyl)-1-propanone, 3-oxo-3-( 1-thiazolyl)propanenitrile, methyl 3-oxo-3-(2-oxazolyl)propanoate, ethyl 3-oxo-3-(1-thiazolyl)propanoate, isopropyl 3-oxo-3-(1thiazolyl)propanoate, tert-butyl 3-oxo-3-(1-thiazolyl)propanoate, 2-ethylhexyl-3-oxo-3-(1-thiazolyl)propanoate, 3-oxo-3-(1-thiazolyl)propanamide, N,N-dimethyl-3-oxo-3-(1-thiazolyl) propanamide, N-methyl-3-oxo-3-(1-thiazolyl)propanamide, N,N-diethyl-3-oxo-3-(1-thiazolyl)propanamide, N-ethyl-3-oxo-3-(1-thiazolyl)propanamide, 3-oxo-3-(N-piperidinyl)-1-( -thiazolyl)-1-propanone, 3-oxo-3-(N-pyrrolidinyl)-1-(1-thiazolyl)-1-propanone, 3-oxo-3-(1-thiazolyl)propanenitrile, methyl 3-oxo-3-(4-oxazolyl)propanoate, ethyl 3-oxo-3-(4-oxazolyl) propanoate, isopropyl 3-oxo-3-(4-oxazolyl)propanoate, tert-butyl 3-oxo-3-(4-oxazolyl)propanoate, 2-ethylhexyl 3-oxo-3-(4-oxazolyl)propanoate, 3-oxo-3-(4-oxazolyl) propanamide, N,N-dimethyl-3-oxo-3-(4-oxazolyl) propanamide, N-methyl-3-oxo-3-(4-oxazolyl)propanamide, N,N-diethyl-3-oxo-3-(4-oxazolyl)propanamide, N-ethyl-3-oxo-3-(4-oxazolyl)propanamide, 3-oxo-3-(N-piperidinyl)-1-(4-oxazolyl)-1-propanone, 3-oxo-3-(N-pyrrolidinyl) 1(4-oxazolyl)-1-propanone, 3-oxo-3-(4-oxazolyl)propanenitrile, methyl 3-oxo-3-(3-pyrazolyl)propanoate, ethyl 3-oxo-3-(3-pyrazolyl)propanoate, isopropyl 3-oxo-3-(3-pyrazolyl)propanoate, tert-butyl 3-oxo-3-(3-pyrazolyl)propanoate, 2-ethylhexyl 3-oxo-3-(3-pyrazolyl)propanoate, 3-oxo-3-(3-pyrazolyl)propanamide, N,N-dimethyl-3-oxo-3-(3-pyrazolyl)propanamide, N-methyl-3-oxo-3-(3-pyrazolyl) propanamide, N,N-diethyl-3-oxo-3-(3-pyrazolyl) propanamide, N-ethyl-3-oxo-3-(3-pyrazolyl)propanamide, 3-oxo-3-(N-piperidinyl)-1-(3-pyrazolyl)-1-propanone, 3-oxo-3-(N-pyrrolidinyl)-1-(3-pyrazolyl)-1-propanone, 3-oxo-3-(3-pyrazolyl)propanenitrile, methyl 3-oxo-3-(4-pyrazolyl)propanoate, ethyl 3-oxo-3-(4-pyrazolyl)-propanoate, isopropyl 3-oxo-3-(4-pyrazolyl)propanoate, tert-butyl 3-oxo-3-(4-pyrazolyl)propanoate, 2-ethylhexyl 3-oxo-3.-(4-pyrazolyl)propanoate, 3-oxo-3-(4-pyrazolyl) propanamide, N,N-dimethyl-3-oxo-3-(4-pyrazolyl) propanamide, N-methyl-3-oxo-3-(4-pyrazolyl) propanamide, N,N-diethyl-3-oxo-3-(4-pyrazolyl) propanamide, N-ethyl-3-oxo-3-(4-pyrazolyl)propanamide, 3-oxo-3-(1-piperidinyl)-1-(4-pyrazolyl)-1-propanone, 3-oxo-3-(N-pyrrolidinyl) -(4-pyrazolyl)-1-propanone, 3-oxo-3-(4-pyrazolyl)propanenitrile, methyl 3-oxo-3-(2-imidazolyl)propanoate, ethyl 3-oxo-3-(2-imidazolyl)propanoate, isopropyl 3-oxo-3-(2-imidazolyl)propanoate, tert-butyl 3-oxo-3-(2-imidazolyl)propanoate, 2-ethylhexyl 3-oxo-3-(2-imidazolyl)propanoate, 3-oxo-3-(2-imidazolyl) propanamide, N,N-dimethyl-3-oxo-3-(2-imidazolyl)propanamide, N-methyl-3-oxo-3-(2-imidazolyl)propanamide, N,N-diethyl-3-oxo-3-(2-imidazolyl)-propanamide, N-ethyl-3-oxo-3-(2-imidazolyl)propanamide, 3-oxo-3-(N-piperidinyl)-1-(2-imidazolyl)-1-propanone, 3-oxo-3-(N-pyrrolidinyl)-1-(2-imidazolyl)-1-propanone, 3-oxo-3-(2-imidazolyl) propanenitrile, methyl 3-oxo-3-(4-imidazolyl)propanoate, ethyl 3-oxo-3-(4-imidazolyl)propanoate, isopropyl 3-oxo-3-(4-imidazolyl)propanoate, tert-butyl 3-oxo-3-(4-imidazolyl) propanoate, 2-ethylhexyl 3-oxo-3-(4-imidazolyl)propanoate, 3-oxo-3-(4-imidazolyl)propanamide, N,N-dimethyl-3-oxo-3-(4-imidazolyl)propanamide, N-methyl-3-oxo-3-(4-imidazolyl)propanamide, N,N-diethyl-3-oxo-3-(4-imidazolyl) propanamide, N-ethyl-3-oxo-3-(4-imidazolyl)propanamide, 3-oxo-3-(N-piperidinyl)-1-(4-imidazolyl)-1-propanone, 3-oxo-3-(N-pyrrolidinyl)-1-(4-imidazolyl)-1-propanone, 3-oxo-3-(4-imidazolyl)propanenitrile, methyl 3-oxo-3-(5-imidazolyl)propanoate, ethyl 3-oxo-3-(5-imidazolyl)propanoate, isopropyl 3-oxo-3-(5-imidazolyl)propanoate, tert-butyl 3-oxo-3-(5-imidazolyl)propanoate, 2-ethylhexyl 3-oxo-3-(5-imidazolyl)propanoate, 3-oxo-3-(5-imidazolyl) propanamide, N,N-dimethyl-3-oxo-3-(5-imidazolyl)propanamide, N-methyl-3-oxo-3-(5-imidazolyl)propanamide, N,N-diethyl-3-oxo-3-(5-imidazolyl) propanamide, N-ethyl-3-oxo-3-(5-imidazolyl)propanamide, 3-oxo-3-(N-piperidinyl)-1-(5-imidazolyl)-1-propanone, 3-oxo-3-(N-pyrrolidinyl)-1-(5-imidazolyl)-1-propanone, 3-oxo-3-(5-imidazolyl) propanenitrile, methyl 3-oxo-3-(3-furanyl)propanoate, ethyl 3-oxo-3-(3-furanyl)propanoate, isopropyl 3-oxo-3-(3-furanyl)propanoate, tert-butyl 3-oxo-3-(3-furanyl)propanoate, 2-ethylhexyl 3-oxo-3-(3-furanyl)propanoate, 3-oxo-3-(3-furanyl)propanamide, N,N-dimethyl-3-oxo-3-(3-furanyl) propanamide, N-methyl-3-oxo-3-(3-furanyl)propanamide, N,N-diethyl-3-oxo-3-(3-furanyl)propanamide, N-ethyl-3-oxo-3-(3-furanyl)propanamide, 3-oxo-3-(N-piperidinyl)-1-(3-furanyl)-1-propanone, 3-oxo-3-(N-pyrrolidinyl)-1-(3-furanyl)-1-propanone, 3-oxo-3-(3-furanyl)propanenitrile, methyl 3-oxo-3-(2-furanyl)propanoate, ethyl 3-oxo-3-(2-furanyl)propanoate, isopropyl 3-oxo-3-(2-furanyl)propanoate, tert-butyl 3-oxo-3-(2-furanyl)propanoate, 2-ethylhexyl 3-oxo-3-(2-furanyl)propanoate, 3-oxo-3-(2-furanyl)propanamide, N,N-dimethyl-3-oxo-3-(2-furanyl)propanamide, N-methyl-3-oxo-3-(2-furanyl)propanamide, N,N-diethyl-3-oxo-3-(2-furanyl )propanamide, N-ethyl-3-oxo-3-(2-furanyl)propanamide, 3-oxo-3-(N-piperidinyl)-1-(2-furanyl)-1-propanone, 3-oxo-3-(N-pyrrolidinyl)-1-(2-furanyl)-1-propanone, 3-oxo-3-(2-furanyl)propanenitrile, methyl 3-oxo-3-(3-indolyl)propanoate, ethyl 3-oxo-3-(3-indolyl)propanoate, isopropyl 3-oxo-3-(3-indolyl)propanoate, tert-butyl 3-oxo-3-(3-indolyl)propanoate, 2-ethylhexyl 3-oxo-3-(3-indolyl)propanoate, 3-oxo-3-(3-indolyl)propanamide, N,N-dimethyl-3-oxo-3-(3-indolyl)propanamide, N-methyl-3-oxo-3-(3-indolyl)propanamide, N,N-diethyl-3-oxo-3-(3-indolyl)propanamide, N-ethyl-3-oxo-3-(3-indolyl) propanamide, 3-oxo-3-(N-piperidinyl)-1-(3-indolyl)-1-propanone, 3-oxo-3-(N-pyrrolidinyl)-1-(3-indolyl)-1-propanone, 3-oxo-3-(3-indolyl)propanenitrile, methyl 3-oxo-3-(2-indolyl)-propanoate, ethyl 3-oxo-3-(2-indolyl) propanoate, isopropyl 3-oxo-3-(2-indolyl)propanoate, tert-butyl 3-oxo-3-(2-indolyl)propanoate, 2-ethylhexyl 3-oxo-3-(2-indolyl)propanoate, 3-oxo-3-(2-indolyl)propanamide, N,N-dimethyl-3-oxo-3-(2-indolyl)propanamide, N-methyl-3-oxo-3-(2-indolyl)propanamide, N,N-diethyl-3-oxo-3-(2-indolyl)propanamide, N-ethyl-3-oxo-3-(2-indolyl)propanamide, 3-oxo-3-(N-piperidinyl)-1-(2-indolyl)-1-propanone, 3-6oxo-3-(N-pyrrolidinyl)-1-(2-indolyl)-1-propanone, 3-oxo-3-(2-indolyl)propanenitrile, methyl 3-oxo-3-(3-benzofuranyl)propanoate, ethyl 3-oxo-3-(3-benzofuranyl)propanoate, isopropyl 3-oxo-3-(3-benzofuranyl)propanoate, tert-butyl 3-oxo-3-(3-benzofuranyl) propanoate, 2-ethylhexyl 3-oxo-3-(3-benzofuranyl)propanoate, 3-oxo-3-(3-benzofuranyl)propanamide, N,N-dimethyl-3-oxo-3-(3-benzofuranyl)propanamide, N-methyl-3-oxo-3-(3-benzofuranyl)propanamide, N,N-diethyl-3-oxo-3-(3-benzofuranyl)propanamide, N-ethyl-3-oxo-3-(3-benzofuranyl)propanamide, 3-oxo-3-(N-piperidinyl)-1-(3-benzofuranyl)-1-propanone, 3-oxo-3-(N-pyrrolidinyl)-1-(3-benzofuranyl)-1-propanone, 3-oxo-3-(3-benzofuranyl)propanenitrile, methyl 3-oxo-3-(2-benzofuranyl)propanoate, ethyl 3-oxo-3-(2-benzofuranyl)propanoate, isopropyl 3-oxo-3-(2-benzofuranyl)propanoate, tert-butyl 3-oxo-3-(2-benzofuranyl)propanoate, 2-ethylhexyl 3-oxo-3-(2-benzofuranyl)propanoate, 3-oxo-3-(2-benzofuranyl)propanamide, N,N-dimethyl-3-oxo-3-(2-benzofuranyl)propanamide, N-methyl-3-oxo-3-(2,benzofuranyl)propanamide, N,N-diethyl-3-oxo-3-(2-benzofuranyl)propanamide, N-ethyl-3-oxo-3-(2-benzofuranyl) propanamide, 3-oxo-3-(N-piperidinyl)-1-(2-benzofuranyl)-1-propanone, 3-oxo-3-(N-pyrrolidinyl)-1-(2-benzofuranyl)-1-propanone, 3-oxo-3-(2-benzofuranyl)propanenitrile, methyl 3-(2-benzothiophenyl)-3-oxopropanoate, ethyl 3-oxo-3-(2-benzothiophenyl)propanoate, isopropyl 3-oxo-3-(2-benzothiophenyl)propanoate, tert-butyl 3-oxo-3-(2-benzothiophenyl)propanoate, 2-ethylhexyl 3-oxo-3-(2-benzothiophenyl)propanoate, 3-oxo-3-(2-benzothiophenyl)propanamide, N,N-dimethyl-3-oxo-3-(2-benzothiophenyl)propanamide, N-methyl-3-oxo-3-(2-benzothiophenyl)propanamide, N,N-diethyl-3-oxo-3-(2-benzothiophenyl)propanamide, N-ethyl -oxo-3-(2-benzothiophenyl)propanamide, 3-oxo-3-(N-piperidinyl)-1-(2-benzothiophenyl)-1-propanone, 3-oxo-3-(N-pyrrolidinyl)-1-(2-benzothiophenyl)-1-propanone, 3-oxo-3-(2-benzothiophenyl)propanenitrile, methyl 3-(3-benzothiophen-yl)-3-oxopropanoate, ethyl 3-oxo-3-(3-benzothiophenyl)propanoate, isopropyl 3-oxo-3-(3-benzothiophenyl)propanoate, tert-butyl 3-oxo-3-(3-benzothiophen-yl)propanoate, 2-ethylhexyl 3-oxo-3-(3-benzothiophenyl)propanoate, 3-oxo-3-(3-benzothiophenyl) propanamide, N,N-dimethyl-3-oxo-3-(3-benzothiophenyl)-propanamide, N-methyl-3-oxo-3-(3-benzothiophenyl)propanamide, N,N-diethyl-3-oxo-3-(3-benzothiophenyl) propanamide, N-ethyl-3-oxo-3-(3-benzothiophenyl)-propanamide, 3-oxo-3-(N-piperidinyl) 1-(3-benzothiophenyl)-1-propanone, 3-oxo-3-(N-pyrrolidinyl)-1-(3-benzothiophenyl)-1-propanone, 3-oxo-3-(3-benzothiophenyl)propanenitrile, methyl 3-(2-quinolinyl)-3-oxopropanoate, ethyl 3-oxo-3-(2-quinolinyl)propanoate, isopropyl 3-oxo-3-(2-quinolinyl)propanoate, tert-butyl 3-oxo-3-(2-quinolinyl)propanoate, 2-ethylhexyl 3-oxo-3-(2-quinolinyl)propanoate, 3-oxo-3-(2-quinolinyl)propanamide, N,N-dimethyl-3-oxo-3-(2-quinolinyl)propanamide, N-methyl-3-oxo-3-(2-quinolinyl)propanamide, N,N-diethyl-3-oxo-3-(2-quinolinyl)propanamide, N-ethyl-3-oxo-3-(2-quinolinyl)propanamide, 3-oxo-3-(N-piperidinyl)-1-(2-quinolinyl)-1-propanone, 3-oxo-3-(N-pyrrolidinyl)-1-(2-quinolinyl)-1-propanone, 3-oxo-3-(2-quinolinyl)-propanenitrile, methyl 3-(3-quinolinyl)-3-oxopropanoate, ethyl 3-oxo-3-(3-quinolinyl)propanoate, isopropyl 3-oxo-3-(3-quinolinyl)propanoate, tert-butyl 3-oxo-3-(3-quinolinyl) propanoate, 2-ethylhexyl 3-oxo-3-(3-quinolinyl)propanoate, 3-oxo-3-(3-quinolinyl)propanamide, N,N-dimethyl-3-6oxo-3-(3-quinolinyl)propanamide, N-methyl-3-oxo-3-(3-quinolinyl)propanamide, N,N-diethyl-3-oxo-3-(3-quinolinyl)propanamide, N-ethyl-3-oxo-3-(3-quinolinyl)propanamide, 3-oxo-3-(N-piperidinyl)-1-(3-quinolinyl)-1-propanone, 3-oxo-3-(N-pyrrolidinyl)-1-(3-quinolinyl)-1-propanone, 3-oxo-3-(3-quinolinyl)-propanenitrile, methyl 3-(3-isoquinolinyl)-3-oxopropanoate, ethyl 3-oxo-3-(3-isoquinolinyl)propanoate, isopropyl 3 oxo-3-(3-isoquinolinyl)propanoate, tert-butyl 3-oxo-3-(3-isoquinolinyl)propanoate, 2-ethylhexyl 3-oxo-3-(3-isoquinolinyl)propanoate, 3-oxo-3-(3-isoquinolinyl)propanamide, N,N-dimethyl-3-oxo-3-(3-isoquinolinyl)propanamide, N-methyl-3-oxo-3-(3-isoquinolinyl)propanamide, N,N-diethyl-3-oxo 3-(3-isoquinolinyl) propanamide, N-ethyl-3-oxo-3-(3-isoquinolinyl) propanamide, 3-oxo-3-(N-piperidinyl)-1-(3-isoquinolinyl)-1-propanone, 3-oxo-3-(N-pyrrolidinyl)-1-(3-isoquinolinyl)-1-propanone, 3-oxo-3-(3-isoquinolinyl)propanenitrile, and even greater preference is given to methyl 3-oxo-3-(2-thiophen-yl)propanoate and ethyl 3-oxo-3-(2-thiophenyl) propanoate.

The process according to the invention is carried out in the presence of a ruthenium-containing catalyst.

For example and with preference, the catalysts used are those which comprise ruthenium complexes. Preferred ruthenium complexes are those which are obtainable by reacting compounds of the formula-(II) with compounds of the formula (III), or complexes of the formula (IV). Particular preference is given to using those ruthenium complexes which are obtainable by reacting compounds of the formula (II) with compounds of the formula (III). In a preferred embodiment, the molar ratio of compounds of the formula (III) to compounds of the formula (II) is 2:1 to 3:1, more preferably 2.01:1 to 2.4:1.

Advantageously, compounds of the formula (III) and compounds of the formula (II) are mixed and the mixture is taken up in organic solvent. Before being added to the reaction mixture, the resulting mixture may also be admixed with a base, preferably a tertiary amine and stirred, for example and with preference, for 10 to 30 min, the molar amount of tertiary amine being, for example and with preference, 1:1 to 3:1, particularly preferably 1:1to 2:1, based on compounds of the formula (III).

For organic solvents and tertiary amines, the same statements and preferred ranges apply as will be described in detail below.

In the compounds of the formula (II)

   (II)

arene is a coordinated aromatic compound having 6 to 12 ring carbon atoms which may further be substituted by up to 6 radicals, each of which is independently selected from the group of $C_1$-$C_8$-alkyl, benzyl and phenyl and X is, for example and with preference, chlorine, bromine or iodine, more preferably chlorine.

Arene is preferably benzene or naphthalene which may be substituted by up to 6 radicals, each of which is selected independently from the group of methyl, ethyl, n-propyl, isopropyl and tert-butyl.

Arene is preferably mesitylene, cumene or benzene.

Particularly preferred compounds of the formula (II) are (benzene)dichlororuthenium dimer, (mesitylene)dichlororuthenium dimer and (cumene)dichlororuthenium dimer, and even greater preference is given to (cumene)dichlororuthenium dimer.

In the formula (III)

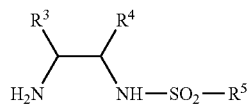   (III)

$R^3$ and $R^4$ are each independently, for example, $C_1$-$C_{20}$-alkyl, $C_4$-$C_{15}$-aryl or $C_5$-$C_{16}$-arylalkyl, or $R^3$ and k4 together are a straight-chain or branched $C_3$-$C_{12}$-alkylene radical, and $R^5$ is $C_1$-$C_{20}$-alkyl, $C_1$-$C_{20}$-fluoroalkyl or $C_4$-$C_{15}$-aryl.

$R^3$ and $R^4$ are preferably identical and are each phenyl or are together straight-chain $C_3$-$C_8$-alkylene, for example 1,3-pentylene or 1,4-butylene, and $R^3$ and $R^4$ are particularly preferably identical and are each phenyl.

$R^5$ is preferably $C_1$-$C_4$-alkyl, $C_1$-$C_4$-fluoroalkyl, phenyl or naphthyl which may be substituted by no, one, two;, three, 6.four or five radicals which are selected from the group of $C_1$-$C_4$-alkyl, $C_1$-$C_4$-alkoxy, $C_1$-$C_4$-fluoroalkyl, fluorine and chlorine.

$R^5$ is particularly preferably methyl, trifluoromethyl, pentafluoroethyl, nona-fluorobutyl, phenyl, p-tolyl, p-ethylphenyl, p-anisyl, p-ethoxyphenyl, p-chlorophenyl, 2,4,6-trimethylphenyl, 2,4,6-triisopropylphenyl, p-fluorophenyl, pentafluorophenyl and naphthyl.

$R^5$ is very particularly preferably p-tolyl, phenyl and naphthyl.

$R^5$ is even more very particularly preferably p-tolyl.

The compounds of the formula (III) preferably had a stereoisomeric purity of 90% or more, particularly preferably of 95% or more and very particularly preferably of 98.5% or more.

Compounds of the formula (III) include:
N-[(1R,2R) and (1S,2S)-2-amino-1,2-diphenylethyl]-p-tolylsulphonamide,
N-[(1R,2R) and (1S,2S)-2-amino-1,2-diphenylethyl]-o-tolylsulphonamide,
N-[(1R,2R) and (1S,2S)-2-amino-1,2-diphenylethyl]-m-tolylsulphonamide,
N-[(1R,2R) and (1S,2S)-2-amino-1,2-diphenylethyl]phenylsulphonamide,
N-[(1R,2R) and (1S,2S)-2-amino-1,2-diphenylethyl]-4-ethylphenylsulphonamide,
N-[(1R,2R) and (1S,2S)-2-amino-1,2-diphenylethyl]-3-ethylphenylsulphonamide,
N-[(1R,2R) and (1S,2S)-2-amino-1,2-diphenylethyl]-2-ethylphenylsulphonamide, N-[(1R,2R) and (1S,2S)-2-amino-1,2-diphenylethyl]-2,4,6-trimethylphenyl-sulphonamide,
N-[(1R,2R) and (1S,2S)-2-amino-1,2-diphenylethyl]-2,4,6-triisopropylphenylsulphonamide, N-[(1R,2R) and (1S,2S)-2-amino-1,2-diphenylethyl]-4-chlorophenylsulphonamide, N-[(1R,2R) and (1S,2S)-2-amino-1,2-diphenylethyl]-3-chlorophenylsulphonamide, N-[(1R,2R) and (1S,2S)-2-amino-1,2-diphenylethyl]-2-chlorophenylsulphonamide, N-[(1R,2R) and (1S,2S)-2-amino-1,2-diphenylethyl]-4-fluorophenylsulphonamide, N-[(1R,2R) and (1S,2S)-2-amino-1,2-diphenylethyl]-3-fluorophenylsulphonamide, N-[(1R,2R) and (1S,2S)-2-amino-1,2-diphenylethyl]-2-fluorophenylsulphonamide, N-[(1R,2R) and (1S,2S)-2-amino-1,2-diphenylethyl]-4-methoxyphenylsulphonamide, N-[(1R,2R) and (1S,2S)-2-amino-1,2-diphenylethyl]-3-methoxyphenylsulphonamide, N-[(1R,2R) and (1S,2S)-2-amino-1,2-diphenylethyl]-2-methoxyphenyl-sulphonamide, N-[(1R,2R) and (1S,2S)-2-amino-1,2-diphenylethyl]-1-naphthylsulphonamide, N-[(1R,2R) and (1S,2S),-2-amino-1,2-diphenylethyl]-2-naphthylsulphonamide, N-[(1R;2R) and (1S,2S)-2-amino-1,2-diphenylethyl]-pentafluorophenylsulphonamide, N-[(1R,2R) and (1S,2S)-2-amino-1,2-diphenylethyl]-methanesulphonamide, N-[(1R,2R) and (1S,2S)-2-amino-1,2-diphenylethyl]-trifluoromethanesulphonamide,
N-[(1R,2R) and (1S,2S)-2-aminocyclohexyl]-p-tolylsulphonamide, N-[( 1R,2R) and (1S,2S)-2-aminocyclohexyl]-o-tolylsulphonamide, N-[(1R,2R) and (1S,2S)-2-aminocyclohexyl]-m-tolylsulphonamide, N-[(1R,2R) and (1S,2S)-2-aminocyclohexyl]-phenylsulphonamide,
N-[(1R,2R) and (1S,2S)-2-aminocyclohexyl]-4-ethylphenylsulphonamide, N-[(1R,2R) and (1S,2S)-2-aminocyclohexyl]-3-ethylphenylsulphonamide, N-[(1R,2R) and (1S,2S)-2-aminocyclohexyl]-2-ethylphenylsulphonamide,
N-[(1R,2R) and (1S,2S)-2-aminocyclohexyl]-2,4,6-trimethylphenylsulphonamide, N-[(1R,2R) and (1S,2S)-2-aminocyclohexyl]-2,4,6-triisopropylphenylsulphonamide, N-[(1R,2R) and (1S,2S)-2-aminocyclohexyl]-4-chlorophenylsulphonamide, N-[(1R,2R) and (1S,2S)-2-aminocyclohexyl]-3-chlorophenylsulphonamide, N-[(1R,2R) and (1S,2S)-2-aminocyclohexyl]-2-chlorophenylsulphonamide, N-[(1R,2R) and (1S,2S)-2-aminocyclohexyl]-4-fluorophenylsulphonamide, N-[(1R,2R) and (1S,2S)-2-aminocyclohexyl]-3-fluorophenylsulphonamide, N-[(1R,2R) and (1S,2S)-2-aminocyclohexyl]-2-fluorophenylsulphonamide, N-[(1R,2R) and (1S,2S)-2-aminocyclohexyl]-4-methoxyphenylsulphonamide, N-[(1R,2R) and (1S,2S)-2-aminocyclohexyl]-3-methoxyphenylsulphonamide,
N-[(1R,2R) and (1S,2S)-2-aminocyclohexyl]-2-methoxyphenylsulphonamide, N-[(1R,2R) and (1S,2S)-2-aminocyclohexyl]-1-naphthylsulphonamide, N-[(1R,2R) and (1S,2S)-2-aminocyclohexyl]-2-naphthylsulphonamide,
N-[(1R,2R) and (1S,2S)-2-aminocyclohexyl]-pentafluorophenylsulphonamide, N-[(1R,2R) and (1S,2S)-2-aminocyclohexyl]-methanesulphonamide, N-[(1R,2R) and (1S,2S)-2-aminocyclohexyl]-trifluoromethanesulphonamide, N-[(1R,2R) and (1S,2S)-2-aminocyclopentyl]-p-tolylsulphonamide, N-[(1R,2R) and (1S,2S)-2-aminocyclopentyl]-o-tolylsulphonamide, N-[(1R,2R) and (1S,2S)-2-aminocyclopentyl]-m-tolylsulphonamide, N-[(1R,2R) and (1S,2S)-2-aminocyclopentyl]-phenylsulphonamide, N-[(1R,2R) and (1S,2S)-2-aminocyclopentyl]-4-ethylphenylsulphonamide, N-[(1R,2R) and (1S,2S)-2-aminocyclopentyl]-3-ethylphenylsulphonamide, N-[(1R,2R) and (1S, 2S)-2-aminocyclopentyl]-2-ethylphenylsulphonamide, N-[(1R,2R) and (1S,2S)-2-aminocyclopentyl]-2,4,6-trimethylphenylsulphonamide, N-[(1R,2R) and (1S,2S)-2-aminocyclopentyl]-2,4,6-triisopropylphenylsulphonamide, N-[(1-R,2R) and (1S,2S)-2-aminocyclopentyl]-4-chlorophenylsulphonamide, N-[(1R,2R) and (1S,2S)-2-aminocyclopentyl]-3-chlorophenylsulphonamide, N-[(1R,2R) and (1S,2S)-2-aminocyclopentyl]-2-chlorophenylsulphonamide, N-[(1R,2R) and (1S,2S)-2-aminocyclopentyl]-4-fluorophenylsulphonamide, N-[(1R,2R) and (1S,2S)-2-aminocyclopentyl]-3-fluorophenylsulphonamide, N-[(1R,2R) and (1S,2S)-2-aminocyclopentyl]-2-fluorophenylsulphonamide, N-[(1R,2R) and (1S,2S)-2-aminocyclopentyl]-4-methoxyphenylsulphonamide, N-[(1R,2R) and (1S,2S)-2-aminocyclopentyl]-3-methoxyphenylsulphonamide, N-[(1R,2R) and (1S,2S)-2-aminocyclopentyl]-2-methoxyphenylsulphonamide, N-[(1R, 2R) and (1S,2S)-2-aminocyclopentyl]-1-naphthylsulphonamide, N-[(1R,2R) and (1S,2S)-2-aminocyclopentyl]-2-naphthylsulphonamide, N-[(1R,2R) and (1S,2S)-2-amino-cyclopentyl]-pentafluorophenylsulphonamide, N-[(1R,2R) and (1S,2S)-2-amino-cyclopentyl]-methansulphonamide, N-[(1R,2R) and (1S,2S)-2-aminocyclopentyl]trifluoromethanesulphonamide.

In the formula (IV)

$$[RuX_2(arene)\{(III)\}] \qquad (IV)$$

arene and X each have the definitions and preferred ranges given under formula (II) and (III) in the formula (IV) represents compounds of the formula (III) having the definitions and preferred ranges given there.

Compounds of the formula (IV) include:

[N-[(1R,2R and 1S,2S)-2-(amino-κN)-1,2-diphenylethyl]-p-tolylsulphonamidato-κN]chloro[(η⁶)-cumene]ruthenium (II)

[N-[(1R,2R and 1S,2S)-2-(amino-κN)-1,2-diphenylethyl]-o-tolylsulphonamidato-κN]chloro[(η⁶)-cumene]ruthenium (II)

[N-[(1R,2R and 1S,2S)-2-(amino-κN)-1,2-diphenyl ethyl]-m-tolylsulphonamidato-κN]chloro[(η⁶)-cumene]ruthenium(II)

[N-[(1R,2R and 1S,2S)-2-(amino-κN)-1,2-diphenylethyl] phenylsulphonamidato-κN]chloro[(η⁶)-cumene]ruthenium(II)

[N-[(1R,2R and 1S,2S)-2-(amino-κN)-1,2-diphenylethyl]-4-ethylphenylsulphonamidato-κN]chloro[(η⁶)-cumene]ruthenium(II)

[N-[(1R,2R and 1S,2S)-2-(amino-κN)-1,2-diphenylethyl]-3-ethylphenylsulphonamidato-κN]chloro[(η⁶)-cumene]ruthenium(II)

[N-[(1R,2R and 1S,2S)-2-(amino-κN)-1,2-diphenylethyl]-2-ethylphenylsulphonamidato-κN]chloro[(η⁶)-cumene]ruthenium(II)

[N-[(1R,2R and 1S,2S)-2-(amino-κN)-1,2-diphenylethyl]-2,4,6-trimethylphenyl-sulphonamidato-κN]chloro[(η⁶)-cumene]ruthenium(II)

[N-[(1R,2R and 1S,2S)-2-(amino-κN)-1,2-diphenylethyl]-2,4,6-triisopropyl-phenylsulphonamidato-κN]chloro[(η⁶)-cumene]ruthenium(II)

[N-[(1R,2R and 1S,2S)-2-(amino-κN)-1,2-diphenylethyl]-4-chlorophenylsulphonamidato-κN]chloro[(η⁶)-cumene]ruthenium(II)

[N-[(1R,2R and 1S,2S)-2-(amino-κN)-1,2-diphenylethyl]-3-chlorophenylsulphonamidato-κN]chloro[(η⁶)-cumene]ruthenium(II)

[N-[(1R,2R and 1S,2S)-2-(amino-κN)-1I,2-diphenylethyl]-2-chlorophenylsulphonamidato-κN]chloro [(η⁶)-cumene]ruthenium(II)

[N-[(1R,2R and 1S,2S)-2-(amino-κN)-1,2-diphenylethyl]-4-fluorophenylsulphonamidato-κN]chloro[(η⁶)-cumene]ruthenium(II)

[N-[(1R,2R and 1S,2S)-2-(amino-κN)-1,2-diphenylethyl]-3-fluorophenylsulphonamidato-κN]chloro[(η⁶)-cumene]ruthenium(II)

[N-[(1R,2R and 1S,2S)-2-(amino-κN)-1,2-diphenylethyl]-2-fluorophenylsulphonamidato-κN]chloro[(η⁶)-cumene]ruthenium(II)

[N-[(1R,2R and 1S,2S)-2-(amino-κN)-1,2-diphenylethyl]-4-methoxyphenylsulphonamidato-κN]chloro[(η⁶)-cumene]ruthenium(II)

[N-[(1R,2R and 1S,2S)-2-(amino-κN)-1,2-diphenylethyl]-3-methoxyphenylsulphonamidato-κN]chloro[(κ⁶)-cumene]ruthenium(II)

[N-[(1R,2R and 1S,2S)-2-(amino-κN)-1,2-diphenylethyl]-2-methoxyphenylsulphonamidato-κN]chloro[(η⁶)-cumene]ruthenium(II)ato-κN]chloro[(η⁶)-cumene]ruthenium(II)

[N-[(1R,2R and 1S,2S)-2-(amino-κN)-1,2-diphenylethyl]-1-naphthylsulphonamidato-κN]chloro[(-q⁶)-cumene]ruthenium(II)

[N-[(1R,2R and 1S,2S)-2-(amino-κN)-1,2-diphenylethyl]-2-naphthylsulphonamidato-κN]chloro[(η⁶)-cumene]ruthenium(II)

[N-[(1R,2R and 1S,2S)-2-(amino-κN)-1,2-diphenylethyl] pentafluorophenylsulphonamidato-κN]chloro[(η⁶)-cumene]ruthenium(II)

[N-[(1R,2R and 1S,2S)-2-(amino-κN)-1,2-diphenylethyl] methanesulphonamidato-κN]chloro[(η⁶)-cumene]ruthenium(II)

[N-[(1R,2R and 1S,2S)-2-(amino-κN)-1,2-diphenylethyl]trifluoromethanesulphonamidato-κN]chloro[(η⁶)-cumene]ruthenium(II)

[N-[(1R,2R and 1S,2S)-2-(amino-κN)-1,2-diphenylethyl]-p-tolylsulphonamidato-κN]chloro [(η⁶) 1,3,5-trimethylbenzene]ruthenium(II)

[N-[(1R,2R and 1S,2S)-2-(amino-κN)-1,2-diphenylethyl]-o-tolylsulphonamidato-κN]chloro[(η⁶)-1,3,5-trimethylbenzene]ruthenium(II)

[N-[(1R,2R and 1S,2S)-2-(amino-κN)-1,2-diphenylethyl]-m-tolylsulphonamidato-κN]chloro [(η⁶) 1,3,5-trimethylbenzene]ruthenium(II)

[N-[(1R,2R and 1S,2S)-2-(amino-κN)-1,2-diphenylethyl] phenylsulphonamidato-κN]chloro[(η⁶)-1,3,5-trimethylbenzene]ruthenium(II)

[N-[(1R,2R and 1S,2S)-2-(amino-κN)-1,2-diphenylethyl]-4-ethyl-phenylsulphonamidato-κN]chloro[(η⁶)-1,3,5-trimethylbenzene]ruthenium(II)

[N-[(1R,2R and 1S,2S)-2-(amino-κN)-1,2-diphenylethyl]-3-ethylphenylsulphonamidato-κN]chloro[(η⁶)-1,3,5-trimethylbenzene]ruthenium(II)

[N-[(1R,2R and 1S,2S)-2-(amino-κN)-1,2-diphenylethyl]-2-ethylphenylsulphonamidato-κN]chloro [(η⁶)-1,3,5-trimethylbenzene]ruthenium(II)

[N-[(1R,2R and 1S,2S)-2-(amino-κN)-1,2-diphenylethyl]-2,4,6-trimethylphenyl-sulphonamidato-κN]chloro[(η⁶)-1,3,5-trimethylbenzene]ruthenium(II)

[N-[(1R,2R and 1S,2S)-2-(amino-κN)-1,2-diphenylethyl]-2,4,6-triisopropyl-phenylsulphonamidato-κN]chloro [(η6)-1,3,5-trimethylbenzene]ruthenium(II)

[N-[(1R,2R and 1S,2S)-2-(amino-κN)-1,2-diphenylethyl]-4-chlorophenylsulphonamidato-κN]chloro[(η⁶)-1,3,5-trimethylbenzene]ruthenium(II)

[N-[(1R,2R and 1S,2S)-2-(amino-κN)-1,2-diphenylethyl]-3-chlorophenylsulphonamidato-κN]chloro[($\eta^6$)-1,3,5-trimethylbenzene]ruthenium(II)

[N-[(1R,2R and 1S,2S)-2-(amino-κN)-1,2-diphenylethyl]-2-chlorophenylsulphonamidato-κN]chloro[($\eta^6$)-1,3,5-trimethylbenzene]ruthenium(II)

[N-[(1R,2R and 1S,2S)-2-(amino-κN)-1,2-diphenylethyl]-4-fluorophenylsulphonamidato-κN]chloro[($\eta^6$)-1,3,5-trimethylbenzene]ruthenium(II)

[N-[(1R,2R and 1S,2S)-2-(amino-κN)-1,2-diphenylethyl]-3-fluorophenyl-sulphonamidato-κN]chloro[($\eta^6$)-1,3,5-trimethylbenzene]ruthenium(II)

[N-[(1R,2R and 1S,2S)-2-(amino-κN)-1,2-diphenylethyl]-2-fluorophenyl-sulphonamidato-κN]chloro[($\eta^6$)-1,3,5-trimethylbenzene]ruthenium(II)

[N-[(1R,2R and 1S,2S)-2-(amino-κN)-1,2-diphenylethyl]-4-methoxy-phenylsulphonamidato-κN]chloro[($\eta^6$)-1,3,5-trimethylbenzene]ruthenium(II)

[N-[(1R,2R and 1S,2S)-2-(amino-κN)-1,2-diphenylethyl]-3-methoxyphenyl-sulphonamidato-κN]chloro[($\eta^6$-)-1,3,5-trimethylbenzene]ruthenium(II)

[N-[(1R,2R and 1S,2S)-2-(amino-κN)-1,2-diphenylethyl]-2-methoxyphenyl-sulphonamidato-κN]chloro [($\eta^6$)-1,3,5 trimethylbenzene]ruthenium(II)ato-κN]chloro[($\eta^6$)-1,3,5-trimethylbenzene]ruthenium(II)

[N-[(1R,2R and 1S,2S)-2-(amino-κN)-1,2-diphenylethyl]-1-naphthylsulphonamidato-κN]chloro[($\eta^6$)-1,3,5-trimethylbenzene]ruthenium(II)

[N-[(1R,2R and 1S,2S)-2-(amino-κN)-1,2-diphenylethyl]-2-naphthylsulphonamidato-κN]chloro[($\eta^6$)-1,3,5-trimethylbenzene]ruthenium(II)

[N-[(1R,2R and 1S,2S)-2-(amino-κN)-1,2-diphenylethyl] pentafluorophenylsulphonamidato-κN]chloro[($\eta^6$) 1,3,5-trimethylbenzene]ruthenium(II)

[N-[(1R,2R and 1S,2S)-2-(amino-κN)-1,2-diphenylethyl] methanesulphonamidato-κN]chloro[($\eta^6$)-1,3,5-trimethylbenzene]ruthenium(II)

[N-[(1R,2R and 1S,2S)-2-(amino-κN)-1,2-diphenylethyl]trifluoromethanesulphonamidato-κN]chloro[($\eta^6$)-1,3,5-trimethylbenzene]ruthenium(II)

[N-[(1R,2R and 1S,2S)-2-(amino-κN)-1,2-diphenylethyl]-p-tolylsulphonamidato-κN]chloro[($\eta^6$)-benzene]ruthenium(II)

[N-[(1R,2R and 1S,2S)-2-(amino-κN)-1,2-diphenylethyl]-o-tolylsulphonamidato-κN]chloro[($\kappa^6$)-benzene]ruthenium(II)

[N-[(1R,2R and 1S,2S)-2-(amino-κN)-1,2-diphenylethyl]-m-tolylsulphonamidato-κN]chloro[($\eta^6$)-benzene]ruthenium(II)

[N-[(1R,2R and 1S,2S)-2-(amino-κN)-1,2-diphenylethyl] phenylsulphonamidato-κN]chloro[($\eta^6$)-benzene]ruthenium(II)

[N-[(1R,2R and 1S,2S)-2-(amino-κN)-1,2-diphenylethyl]-4-ethylphenylsulphonamidato-κN]chloro [($\eta^6$)-benzene]ruthenium(II)

[N-[(1R,2R and 1S,2S)-2-(amino-κN)-1,2-diphenylethyl]-3-ethylphenylsulphonamidato-κN]chloro[($\eta^6$)-benzene]ruthenium(II)

[N-[(1R,2R and 1S,2S)-2-(amino-κN)-1,2-diphenylethyl]-2-ethylphenylsulphonamidato-κN]chloro[($\eta^6$)-benzene]ruthenium(II)

[N-[(1R,2R and 1S,2S)-2-(amino-κN)-1,2-diphenylethyl]-2,4,6-trimethylphenyl-sulphonamidato-κN]chloro[($\eta^6$)-benzene]ruthenium(II)

[N-[(1R,2R and 1S,2S)-2-(amino-κN)-1,2-diphenylethyl]-2,4,6-triisopropylphenylsulphonamidato-κN]chloro[($\eta^6$)-benzene]ruthenium(II)

[N-[(1R,2R and 1S,2S)-2-(amino-κN)-1,2-diphenylethyl]-4-chlorophenylsulphonamidato-κN]chloro[($\eta^6$)-benzene]ruthenium(II)

[N-[(1R,2R and 1S,2S)-2-(amino-κN)-1,2-diphenylethyl]-3-chlorophenylsulphonamidato-κN]chloro[($\eta^6$)-benzene]ruthenium(II)

[N-[(1R,2R and 1S,2S)-2-(amino-κN)-1,2-diphenylethyl]-2-chlorophenylsulphonamidato-κN]chloro[($\eta^6$)-benzene]ruthenium(II)

[N-[(1R,2R and 1S,2S)-2-(amino-κN)-1,2-diphenylethyl]-4-fluorophenylsulphonamidato-κN]chloro[($\eta^6$)-benzene]ruthenium(II)

[N-[(1R,2R and 1S,2S)-2-(amino-κN)-1,2-diphenylethyl]-3-fluorophenylsulphonamidato-κN]chloro[($\eta^6$)-benzene]ruthenium(II)

[N-[(1R,2R and 1S,2S)-2-(amino-κN)-1,2-diphenylethyl]-2-fluorophenylsulphonamidato-κN]chloro[($\eta^6$)-benzene]ruthenium(II)

[N-[(1R,2R and 1S,2S)-2-(amino-κN)-1,2-diphenylethyl]-4-methoxyphenylsulphonamidato-κN]chloro[($\eta^6$)-benzene]ruthenium(II)

[N-[(1R,2R and 1S,2S)-2-(amino-κN)-1,2-diphenylethyl]-3-methoxyphenylsulphonamidato-κN]chloro[($\eta^6$)-benzene]ruthenium(II)

[N-[(1R,2R and 1S,2S)-2-(amino-κN)-1,2-diphenylethyl]-2-methoxyphenylsulphonamidato-κN]chloro [($\eta^6$)-benzene]ruthenium(II)ato-κN]chloro[($\eta^6$)-benzene]ruthenium(II)

[N-[(1R,2R and 1S,2S)-2-(amino-κN)-1,2-diphenylethyl]-1-naphthylsulphonamidato-κN]chloro[($\eta^6$)-benzene]ruthenium(II)

[N-[(1R,2R and 1S,2S)-2-(amino-κN)-1,2-diphenylethyl]-2-naphthylsulphonamidato-κN]chloro[($\eta^6$)-benzene]ruthenium(II)

[N-[(1R,2R and 1S,2S)-2-(amino-κN)-1,2-diphenylethyl] pentafluorophenyl-sulphonamidato-κN]chloro[($\eta^6$)-benzene]ruthenium(II)

[N-[(1R,2R and 1S,2S)-2-(amino-κN)-1,2-diphenylethyl] methanesulphonamidato-κN](chloro[($\eta^6$)-benzene]ruthenium(II)

[N-[(1R,2R and 1S,2S)-2-(amino-κN)-1,2-diphenylethyl]trifluoromethanesulphonamidato-κN]chloro[($\eta^6$)-benzene]ruthenium(II)

[N-[(1R,2R and 1S,2S)-2-(amino-κN)-cyclohexyl]-p-tolyl-sulphonamidato-κN]chloro[($\eta^6$)-benzene]ruthenium(II)

[N-[(1R,2R and 1S,2S)-2-(amino-κN)-cyclohexyl]-m-tolyl-sulphonamidato-κN]chloro[($\eta^6$)-benzene]ruthenium(II)

[N-[(1R,2R and 1S,2S)-2-(amino-κN)-cyclohexyl]phenyl-sulphonamidato-κN]chloro[($\eta^6$)-benzene]ruthenium(II)

[N-[(1R,2R and 1S,2S)-2-(amino-κN)-cyclohexyl]-4-ethylphenylsulphonamidato-κN]chloro[($\eta^6$)-benzene]ruthenium(II)

[N-[(1R,2R and 1S,2S)-2-(amino-κN)-cyclohexyl]-2,4,6-trimethylphenylsulphonamidato-κN]chloro[($\eta^6$)-benzene]ruthenium(II)

[N-[(1R,2R and 1S,2S)-2-(amino-κN)-cyclohexyl]-4-chlorophenylsulphonamidato-κN]chloro[($\eta^6$)-benzene]ruthenium(II)

[N-[(1R,2R and 1S,2S)-2-(amino-κN)-cyclohexyl]-3-chlorophenylsulphonamidato-κN]chloro[($\eta^6$)-benzene]ruthenium(II)

[N-[(1R,2R and 1S,2S)-2-(amino-κN)-cyclohexyl]-4-fluorophenylsulphonamidato-κN]chloro[($\eta^6$)-benzene]ruthenium(II)

[N-[(1R,2R and 1S,2S)-2-(amino-κN)-cyclohexyl]-3-fluorophenylsulphonamidato-κN]chloro[($\eta^6$)-benzene]ruthenium(II)

[N-[(1R,2R and 1S,2S)-2-(amino-κN)-cyclohexyl]-4-methoxyphenylsulphonamidato-κN]chloro[(η$^6$)-benzene]ruthenium(II)

[N-[(1R,2R and 1S,2S)-2-(amino-κN)-cyclohexyl]-3-methoxyphenylsulphonamidato-κN]chloro[(η$^6$)-benzene]ruthenium(II)

[N-[(1R,2R and 1S,2S)-2-(amino-κN)-cyclohexyl]-1-naphthylsulphonamidato-κN]chloro[(η$^6$)-benzene]ruthenium(II)

[N-[(1R,2R and 1S,2S)-2-(amino-κN)-cyclohexyl]-2-naphthylsulphonamidato-κN]chloro[(η$^6$)-benzene]ruthenium(II)

[N-[(1R,2R and 1S,2S)-2-(amino-κN)-cyclohexyl]methanesulphonamidato-κN]chloro[(η$^6$)-benzene]ruthenium(II)

p1 [N-[(1R,2R and 1S,2S)-2-(amino-κN)-cyclohexyl]trifluoromethanesulphonamidato,-κN]chloro[(η$^6$)-benzene]ruthenium(II)

[N-[(1R,2R and 1S,2S)-2-(amino-κN)-cyclohexyl]-p-tolylsulphonamidato-κN]chloro[(η$^6$)-cumene]ruthenium(II)

[N-[(1R,2R and 1S,2S)-2-(amino-κN)-cyclohexyl]-m-tolylsulphonamidato-κN]chloro[(η$^6$)-cumene]ruthenium(II)

[N-[(1R,2R and 1S,2S)-2-(amino-κN)-cyclohexyl]phenylsulphonamidato-κN]chloro[(η$^6$)-cumene]ruthenium(II)

[N-[(1R,2R and 1S,2S)-2-(amino-κN)-cyclohexyl]-4-ethylphenylsulphonamidato-κN]chloro[(η$^6$)-cumene]ruthenium(II)

[N-[(1R,2R and 1S,2S)-2-(amino-κN -cyclohexyl]-2,4,6-trimethylphenylsulphonamidato-κN]chloro[(η$^6$)-cumene]ruthenium(II)

[N-[(1R,2R and 1S,2S)-2-(amino-κN)-cyclohexyl]-4-chlorophenylsulphonamidato-κN]chloro[(η$^6$)-cumene]ruthenium(II)

[N-[(1R,2R and 1S,2S)-2-(amino-κN)-cyclohexyl]-3-chlorophenylsulphonamidato-κN]chloro[(η$^6$)-cumene]ruthenium(II)

[N-[(1R,2R and 1S,2S)-2-(amino-κN)-cyclohexyl]-4-fluorophenylsulphonamidato-κN]chloro[(η$^6$)-cumene]ruthenium(II)

[N-[(1R,2R and 1S,2S)-2-(amino-κN)-cyclohexyl]-3-fluorophenylsulphonamidato-κN]chloro[(η$^6$)-cumene]ruthenium(II)

[N-[(1R,2R and 1S,2S)-2-(amino-κN)-cyclohexyl]-4-methoxyphenylsulphonamidato-κN]chloro[(η$^6$)-cumene]ruthenium(II)

[N-[(1R,2R and 1S,2S)-2-(amino-κN)-cyclohexyl]-3-methoxyphenylsulphonamidato-κN]chloro[η$^6$)-cumene]ruthenium(II)

[N-[(1R,2R and 1S,2S)-2-(amino-κN)-cyclohexyl]-1-naphthylsulphonamidato-κN]chloro[(η$^6$)-cumene]ruthenium(II)

[N-[(1R,2R and 1S,2S)-2-(amino-κN)-cyclohexyl]-2-naphthylsulphonamidato-κN]chloro[(η$^6$)-cumene]ruthenium(II)

[N-[(1R,2R and 1S,2S)-2-(amino-κN)-cyclohexyl]methanesulphonamidato-κN]chloro[(η$^6$)-cumene]ruthenium(II),

[N-[(1R,2R and 1S,2S)-2-(amino-κN)-cyclohexyl]trifluoromethanesulphonamidato-κN]chloro[(η$^6$)-cumene]ruthenium(II)

[N-[(1R,2R and 1S,2S)-2-(amino-κN)-cyclohexyl]-p-tolylsulphonamidato-κN]chloro[(η$^6$)-1,3 5-trimethylbenzene]ruthenium(II)

[N-[(1R,2R and 1S,2S)-2-(amino-κN)-cyclohexyl]-m-tolylsulphonamidato-κN]chloro[(η$^6$)-1,3,5-trimethylbenzene]ruthenium(II)

[N-[(1R,2R and 1S,2S)-2-(amino-κN)-cyclohexyl]phenylsulphonamidato-κN]chloro[(η$^6$)-1,3,5-trimethylbenzene]ruthenium(II)

[N-[(1R,2R and 1S,2S)-2-(amino-κN)-cyclohexyl]-4-ethylphenylsulphonamidato-κN]chloro[(η$^6$)-1,3,5-trimethylbenzene]ruthenium(II)

[N-[(1R,2R and 1S,2S)-2-(amino-κN)-cyclohexyl] -2,4,6-trimethylphenyl-sulphonamidato-κN]chloro[(η$^6$) 1,3,5-trimethylbenzene]ruthenium(II)

[N-[(1R,2R and 1S,2S)-2-(amino-κN)-cyclohexyl]-4-chlorophenyl-sulphonamidato-κN]chloro[(η$^6$)-1,3,5-trimethylbenzene]ruthenium(II)

[N-[(1R,2R and 1S,2S)-2-(amino-κN)-cyclohexyl]-3-chlorophenyl-sulphonamidato-κN]chloro[(η$^6$)-1,3,5-trimethylbenzene]ruthenium(II)

[N-[(1R,2R and 1S,2S)-2-(amino-κN)-cyclohexyl]-4-fluorophenyl-sulphonamidato-κN]chloro[(η$^6$)-1,3,5-trimethylbenzene]ruthenium(II)

[N-[(1R,2R and 1S,2S)-2-(amino-κN)-cyclohexyl]-3-fluorophenyl-sulphonamidato-κN]chloro[(η$^6$)-1,3,51-trimethylbenzene]ruthenium(II)

[N-[(1R,2R and 1S,2S)-2-(amino-κN)-cyclohexyl]-4-methoxyphenyl-sulphonamidato-κN]chloro[(η$^6$)-1,3,5-trimethylbenzene]ruthenium(II)

[N-[(1R,2R and 1S,2S)-2-(amino-κN)-cyclohexyl]-3-methoxyphenyl-sulphonamidato-κN]chloro[(η$^6$)-1,3,5-trimethylbenzene]ruthenium(II)

[N-[(1R,2R and 1S,2S)-2-(amino-κN)-cyclohexyl]-1-naphthylsulphonamidato-κN]chloro[(η$^6$) 1,3,5-trimethylbenzene]ruthenium(II)

[N-[(1R,2R and 1S,2S)-2-(amino-κN)-cyclohexyl]-2-naphthylsulphonamidato-κN]chloro[(η$^6$)-1,3,5-trimethylbenzene]ruthenium(II)

[N-[(1R,2R and 1S,2S)-2-(amino-κN)-cyclohexyl]methanesulphonamidato-κN]chloro[(η$^6$)-1,3,5-trimethylbenzene]ruthenium(II) and

[N-[(1R,2R and 1S,2S)-2-(amino-κN)-1,3,5-cyclohexyl]trifluoromethanesulphonamidato-κN]chloro[(η$^6$)-1,3,5-trimethylbenzene]ruthenium(II)

Particularly preferred catalysts for the purposes of the invention are those which comprise ruthenium complexes which are obtainable by reacting S,S— or R,R—N-p-toluenesulfonyl-1,2-diphenylethylenediamine with (cumene) dichlororuthenium dimer.

The process according to the invention is carried out in the presence of at least one amine, preferably an amine of which at least some is present in protonated form.

Also, formic acid, formates or mixtures thereof are used for the process according to the invention.

Preference is giving to using mixtures of formic, acid with amines. In this way, the corresponding ammonium formates are at least partially formed and can be used in a similar manner.

Useful amines are in particular those of the formula (V)

$$NR^6R^7R^8 \quad (V)$$

where $R^6$, $R^7$ and $R^8$ are each independently hydrogen, $C_1$-$C_8$-allyl or benzyl.

Particularly preferred amines are ammonia and those of the formula (V) where $R^6$, $R^7$ and $R^8$ are each independently $C_1$-$C_8$-alkyl or benzyl.

Particularly preferred amines are those of the formula (V) where $R^6$, $R^7$ and $R^8$ are identical and are each ethyl, n-butyl or n-hexyl, and even greater preference is given to the use of triethylamine.

The molar ratio of formic acid to tertiary amine may be, for example, 1:1 to 3:1, and preference is given to a ratio of 1.01:1 to 1.5:1.

The molar ratio of formic acid based on substrate used may be, for example, 1:1 to 3:1, and preference is given to 1:1 to 1.5:1, particular preference to 1.02:1 to 1.1:1.

The process according to the invention may be carried out in the presence or absence, preferably in the presence, of organic solvent.

Examples of suitable organic solvents include:

amides, for example dimethylformamide, N-methylpyrrolidinone, optionally halogenated aliphatic or araliphatic solvents having up to 16 carbon atoms, for example toluene, o-, m- and p-xylene, chloroform dichloromethane, chlorobenzene, the isomeric dichlorobenzenes, fluorobenzene, nitrites, for example acetonitrile, benzonitrile, dimethyl sulfoxide or mixtures thereof.

Preferred solvents are acetonitrile, N-methylpyrrolidinone, chloroform, dichloro-methane, chlorobenzene, the isomeric dichlorobenzenes, fluorobenzene or mixtures thereof, and particular preference is given to dichloromethane, acetonitrile, N-methylpyrrolidone or mixtures thereof.

The reaction temperature maybe, for example, −10 to 150° C., and preference is given to 20 to 100° C., particular preference to 20 to 80° C.

The reaction times are, for example, between 0.5 h and 48 h, preferably between 6 and 24 h.

The molar amount of ruthenium may be, for example, 0.01 to 1.0 mol %, based on the substrate used, and preference is given to 0.02 to 0.2 mol %, very particular preference to 0.02 to 0.1 mol %.

It is advantageous, although not obligatory, to carry out the reaction in a substantially oxygen-free atmosphere. Substantially oxygen-free means, for example, a content of 0 to 1% by volume, preferably 0 to 0.1% by volume, of oxygen.

The reaction may be accelerated by removing carbon dioxide which is released during the reaction. Advantageous, and therefore encompassed by the invention, is intensive stirring of the reaction mixture at an average stirrer speed of, for example, 100 to 3,000 $min^{-1}$, preferably 500 to 1,500 $min^{-1}$. Alternatively, or in supplementation thereto, the removal of carbon-dioxide may be supported by passing through or passing over an inert gas stream through or over the reaction mixture. Examples of suitable gases include nitrogen, noble gases, for example argon, or mixtures thereof.

In the manner according to the invention, stereoisomerically enriched 3-heteroaryl-3-hydroxypropionic acid derivatives of the formula (VI)

heteroaryl-CH(OH)—CH$_2$W  (VI)

where heteroaryl and W have the same definitions and preferred ranges as were named under the formula (I) are obtained.

Depending on the choice of the configuration of the ligands, the S- or R-configured products at the 3-position are obtainable.

The stereoisomerically enriched 3-heteroaryl-3-hydroxypropionic acid derivatives which can be prepared according to the invention are suitable in particular for use in a process for preparing liquid-crystalline compounds, agrochemicals and pharmaceuticals or intermediates thereof.

A particularly preferred embodiment of the process according to the invention is described hereinbelow, without imposing any limitation.

In a stirred tank, a 1:1 mixture (molar) of formic acid and triethylamine is prepared by simple mixing and the 3-heteroaryl-3-oxopropionic acid derivative is added to this biphasic mixture in an equimolar amount or a slight deficiency. Depending on the solubility of the substrate, an amount of an organic solvent is added. This mixture is inertized by passing through nitrogen and the mixture is heated to the desired reaction temperature with vigorous stirring.

The catalyst is added to this mixture as a solution in dichloromethane in molar ratios compared to the substrate of, for example, 1:500 to 1:5000, and the reaction mixture is stirred for the desired time. The conversion is followed by chromatography.

The reaction mixture may subsequently be worked up by processes known to those skilled in the art. It has proven advantageous to add solvents and dilute aqueous hydrochloric acid or water to the reaction mixture for workup. After phase separation, the product may be isolated in da-manner known per se from the organic phase either distillatively or by a suitable crystallization process.

The advantage of the present invention is that 3-heteroaryl-3-hydroxypropionic acid derivatives can be obtained in stereoisomerically enriched form in a manner which is efficient and can be performed in a technically simple manner to achieve high yields.

EXAMPLES

General Procedure for the Transfer Hydrogenation of 3-Heteroaryl-3-Oxopropionic Acid Derivatives Examples 1-10

In a Schlenk vessel, the catalyst solution -is prepared by weighing in 2.03 mol equivalents of 1S,2S—N-(p-toluenesulfonyl)-1,2-diphenylethylenediamine (S,S-TsDPEN) and 1 mol equivalent of [(cumene)RuCl$_2$]$_2$, stirring this mixture in 5 ml of CH$_2$Cl$_2$ and admixing with 2 mol equivalents of Et$_3$N for 15 min.

In a 100 ml multi-necked flask equipped with a sparging stirrer, reflux condenser and thermometer, a formic acid/Et$_3$N mixture (molar ratio 1:1, molar ratio 1.05:1 based on the substrate) is prepared by slowly adding HCOOH dropwise to Et$_3$N by a dropping funnel within 5 min with stirring and ice-cooling. The appropriate keto compound is then added to this biphasic mixture (500-5000 eq. based on the catalyst), the homogeneous yellow solution is optionally admixed with solvent, and the entire mixture is degassed by passing through argon for 20 min. It is heated to the target temperature and the dark red catalyst solution is added all at once by syringe to the reaction mixture with vigorous stirring. The mixture is stirred under argon for the stated time.

The mixture is diluted with water and CH$_2$Cl$_2$ and stirred for a further 10 min, and, after phase separation, the H$_2$O phase is extracted 2× with CH$_2$Cl$_2$. The combined organic phases are washed with NaCl solution, dried over MgSO$_4$ and filtered, and then the solvent is removed on a rotary evaporator. The crude product is either distilled and recrystallized, for example from hexane/petroleum ether or from hexane/dichloromethane, or used as a crude mixture in further reactions. The product is obtained in 90-100% yield.

The conversion and enantiomer analysis is effected by gas chromatography.

Methyl 3-hydroxy-3-(4-pyridinyl)propanoate (1)

$^1$H NMR (d1-chloroform, 400 MHz): δ=8.54, 7.35 (each d, each 2H, Py-H, 2J=6 Hz), 5.12 (dd, 1H, CHOH), 3.69 (s, 3H, OCH3), 2.71 (m, 2H, CHH) ppm.

Chiral GC: 15.49, 16.07 min.

Ethyl 3-hydroxy-3-(4-pyridinyl)propanoate (2)

$^1$H NMR (d1-chloroform, 400 MHz): δ=8.54, 7. 32 (each d, each 2H, Py-H, 2J=6 Hz), 5.13 (dd, 1H, CHOH), 4.19 (q, 2H; OCH2), 2.73 (m, 2H, CHH), 1.27 (t, 3H, CH3) ppm.

Chiral GC: 18.33, 18.60 min.

Ethyl 3-hydroxy-3-(3-pyridinyl)propanoate (3)

$^1$H NMR (d1-chloroform, 400 MHz): δ=8.62, 8.61, 7.77, 7.33 (each m, each 1H, Py-H), 5.19 (dd, 1H, CHOH), 3.75 (s, 3H, OCH3), 3.44 (d, 1 H, OH), 2.77 (m, 2H, CHH) ppm.

Chiral GC: 16.69, 17.56 min.

Ethyl (3S) 3-(6-chloro-3-pyridinyl)-3-hydroxypropanoate (4)

$^1$H NMR (d1-chloroform, 400 MHz): δ=8.32 (d, 2H, Py-H, J =2 Hz), 7.66 (dd, 2H, Py-H, J=2 Hz, J=8 Hz), 7.26 (d, 2H, Py-H, J=8 Hz), 5.12 (dd, 1H, CHOH), 4.12 (q, 2H, OCH2), 2.68 (m, 2H, CHH), 1.22 (t, 3H, CH3) ppm.

Chiral GC: 14.12, 14.74 min.

Methyl 3-hydroxy-3-(3-thiophenyl)propanoate (5)

$^1$H NMR (d1-chloroform, 400 MHz): δ=7.30, 7.23, 7.08 (each m, each 1H, Ar—H), 5.22 (dd, 1H, CHOH), 3.72 (s, 3H, OCH3), 2.79 (m, 2H, CHH) ppm.

Chiral GC: 15.56, 15.99 min.

(S)-Methyl 3-hydroxy-3-(2-thiophenyl)propanoate (6)

$^1$H NMR (d1-chloroform, 400 MHz): δ=7.23 (m, 1H, Ar—H), 6.95 (m, 2H, Ar—H), 5.36 (dd, 1H, CHOH), 3.71 (s, 3H, OCH3), 2.86 (m, 2H, CHH) ppm.

$^{13}$C-NMR (d1-chloroform, 100 MHz): δ=185.3 (C=O), 146.8 (C, Ar), 127.1 (CH, Ar), 125.3 (CH, Ar), 124.1 (CH, Ar), 66.9 (CHOH), 52.4 (CH3), 43.5 (CH2) ppm.

Chiral GC: 14.05, 14.41 min.

Methyl 3-(3-chloro-1-benzothien-2-yl)-3-hydroxypropanoate (7)

$^1$H NMR (d1-chloroform, 400 MHz): δ=7.79 (m, 2H, Ar—H), 7.3-7.5 (m, 2H, Ar—H), 5.69 (dd, 1H, CHOH), 3.77 (s, 3H, OCH3) 2.8-3.0 (m, 3H, CHH and OH) ppm.

Chiral GC: 22.74, 23.47 min.

Methyl 3-hydroxy-3-(3-furanyl)propanoate (8)

$^1$H NMR (d1-chloroform, 400 MHz): δ=7.42, 7.39, 6.40 (each m, each 1H, Ar—H), 5.09 (dd, 1H, CHOH), 4.19 (q, 2H, OCH2), 3.30 (br, 1H, OH), 2.73 (m, 2H, CHH), 1.27 (t, 3H, CH3) ppm.

Chiral GC: 5.56, 5.84 min.

Methyl 3-hydroxy-3-(2-furanyl)propanoate (9)

$^1$H NMR (d1-chloroform, 400 MHz): δ=7.39, 6.34, 6.29 (each m, each 1H, Ar—H), 5.14 (dt, 1H, CHOH), 4.21 (q, 2H, OCH2), 3.24 (d, 1H, OH), 2.90 (dd, 2H, CHH), 2.82 (dd, 2H, CHH), 1.28 (t, 3H, CH3) ppm.

Chiral GC: 9.02, 9.25 min.

Ethyl 3-hydroxy-3-(2-pyridinyl)propanoate (10)

$^1$H NMR (d1-chloroform, 400 MHz): δ=8.53, 7.70, 7.42, 7.20 (each m, each 1H, Ar—H), 5.19 (m, 1H, CHOH), 4.18 (q, 2H, OCH2), 2.90 (dd, 1H, CHH), 2.76 (dd, 1H, CHH), 1.25 (t, 3H, CH3) ppm.

Chiral GC (TMS ester): 22.92, 23.52 min.

The results of Examples 1-10 are compiled in Table 1.

TABLE 1

| Example | Time [h] | S/C | Conversion [%] | Enantiomeric excess (ee) [%] |
|---|---|---|---|---|
| 1 | 18 | 500 | 100 | 87.4 |
| 2 | 18 | 500 | 100 | 82.8 |
| 3 | 18 | 500 | 99.2 | 81.9 |
| 4 | 18 | 500 | 100 | 62.5 |
| 5 | 18 | 500 | 100 | 37 |
| 6 | 18 | 500 | 100 | 98.2 (S) |
| 7 | 18 | 500 | 100 | 93.1 |
| 8 | 18 | 500 | 98.7 | 92.3 |
| 9 | 18 | 500 | 99.9 | 96.6 |
| 10 | 18 | 500 | 100 | 88.6 |

Solvent: $CH_2Cl_2$, substrate concentration: 1.6 mol/l, T = 30° C., 1.4 mol equivalents of HCOOH/Et$_3$N (molar ratio 1:1).

Examples 11-15

Solvent influence on the conversation rates (TOF) and enantioselectivities in the reduction of methyl 3-oxo-3-(2-thiophenyl)propanoate.

Procedure of the experiment as in Example 1, but with magnetic stirring.

The results of Examples 11-15 are compiled in Table 2.

TABLE 2

| Example | S/C | Solvent | Average TOF (1 h) | Average TOF (8 h) | Conversion (16 h) | Ee [%] |
|---|---|---|---|---|---|---|
| 11 | 1000 | $CH_2Cl_2$ | 185 | 106 | 100 | 97.4 |
| 12 | 1000 | none | 204 | 108 | 100 | 97.0 |
| 13 | 1000 | NMP | 159 | 112 | 100 | 97.7 |
| 14 | 1000 | $CH_3CN$ | 334 | 115 | 100 | 97.0 |
| 15 | 1000 | DMSO | 152 | 90 | 87, 7 | 97.1 |

Substrate concentration: 2.2 mol/l, T = 40° C., 1.3 mol equivalents of HCOOH/Et$_3$N (molar ratio 1:1).

Examples 16-19

Influence of the removal of $CO_2$ on the conversion and reaction rate in the transferhydrogenation of methyl 3-oxo-3-(2-thiophenyl)propanoate[1].

The results of Examples 16-19 are compiled in Table 3.

TABLE 3

| Example | S/C | Stirring | Sparging | t [h] | C [%] |
|---|---|---|---|---|---|
| 16 | 1500 | magnetic | closed apparatus | 48 | 33 |
| 17 | 1500 | magnetic | passing Ar over | 48 | 80 |
| 18 | 1200 | KPG stirrer | passing Ar over | 17 | 100 |
| 19 | 1200 | KPG stirrer | passing Ar through | 12 | 99 |

Solvent: $CH_2Cl_2$, substrate concentration = 2.5-2.7 mol/l, T = 40° C., 1.07 mol equivalents of HCOOH/Et$_3$N (molar ratio 1:1).

Examples 20-23

Examples 20-23 were carried out in a similar manner to Example 1.

3-Hydroxy-3-(2-furanyl)propanenitrile (20)

$^1$H NMR (D1-chloroform, 400 MHz): δ=7.41 (m, 1H, Ar—H), 6.38, (m, 2H, Ar—H), 5.04 (dd, 1H, CHOH), 3.03 (br, 1H, OH), 2.90 (m, 2H, CHH) ppm.

Chiral GC: 6.47, 7.29 min. ee=94.5%.

(S)-3-Hydroxy-3-(2-thiophenyl)propanenitrile (21)

$^1$H NMR (D1-chloroform, 400 MHz): δ=7.32, 7.08, 7.01 (each m, each 1H, Ar—H), 5.28 (dd, 1H, CHOH), 2.86 (m, 3H, CHH and OH) ppm.

Chiral GC: 13.23, 13.56 min. ee 97.-1%.

3-Hydroxy-3-(3-thiophenyl)propanenitrile (22)

$^1$H NMR (D1-chloroform, 400 MHz): δ=7.37, 7.33, 7.12 (each m, each 1H, Ar—H), 5.12 (dd, 1H, CHOH), 2.80 (m, 2H, CHH) 2.75 (br, 1H, OH) ppm.

Chiral GC: 13.61, 13.97 min. ee=95.9%.

3-Hydroxy-3-(6-chloro-3-pyridinyl)propanenitrile (23)

$^1$H NMR (D1-chloroform, 400 MHz): δ=8.40 (d, 2H, Py-H, J=2 Hz), 7.80 (dd, 2H, Py-H, J=2 Hz, J=8 Hz), 7.37 (d, 2H, Py-H, J=8Hz), 5.14 (dd, 1H, CHOH), 2.82 (m, 2H, CHH) ppm.

Chiral GC: 24.78, 25.14 min. ee=73.3%.

The results of Examples 20-23 are compiled in Table 4.

TABLE 4

| Example | t [h] | S/C | C [%] | ee [%] |
|---------|-------|-----|-------|--------|
| 20 | 20 | 250 | 100 | 94.5 |
| 21 | 20 | 250 | 100 | 97.1 |
| 22 | 20 | 250 | 100 | 95.9 |
| 23 | 20 | 250 | 100 | 73.3 |

Solvent: CH$_2$Cl$_2$, substrate concentration = 0.6 mol/l, T = 35° C., 1.4 mol equivalents of HCOOH/Et$_3$N (molar ratio 1:1).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing ethyl 3-hydroxy-3-(2-thiophenyl)-propanoate from ethyl 3-oxo-3-(2-thiophenyl)-propanoate; methyl 3-hydroxy-3-(2-thiophenyl)-propanoate from methyl 3-oxo-3-(2-thiophenyl)-propanoate;

methyl 3-(3-chloro-1-benzothien-2-yl)-3-hydroxypropanoate from methyl 3-(3-chloro-1-benzothien-2-yl)-3-oxo-propanoate; methyl 3-hydroxy-3-(3-furanyl)-propanoate from methyl 3-oxo-3-(3-furanyl)-propanoate; or methyl 3-hydroxy-3-(2-furanyl)-propanoate from methyl 3-oxo-3-(2-furanyl)-propanoate; said process comprising reacting formic acid, formate or a mixture thereof with said ethyl 3-oxo-3-(2-thiophenyl)-propanoate; said methyl 3-oxo-3-(2-thiophenyl)-propanoate;

said methyl 3-(3-chloro-1-benzothien-2-yl)-3-oxo-propanoate; said methyl 3-oxo-3-(3-furanyl)-propanoate; or said methyl 3-oxo-3-(2-furanyl)-propanoate, wherein in each case said reacting is conducted in the presence of a ruthenium-containing catalyst and in the presence of at least one amine, at least some of which amine is present in protonated form.

2. Process according to claim 1, which comprises preparing methyl 3-hydroxy-3-(2-thiophenyl)-propanoate from methyl 3-oxo-3-(2-thiophenyl)-propanoate.

3. Process according to claim 1, wherein the ruthenium-containing catalyst used is a catalyst which comprises a ruthenium complex.

4. Process according to claim 3, wherein the ruthenium complex is one of the formula (IV) or one obtainable by reacting a compound of the formula (II) with a compound of the formula (III) where, in the compound of the formula (II):

arene is a coordinated aromatic compound having 6 to 12 ring carbon atoms which is optionally substituted by up to 6 radicals, each of which is independently selected from the group consisting of C$_1$-C$_8$-alkyl, benzyl and phenyl, and X is chlorine, bromine or iodine, and where, in the formula (III):

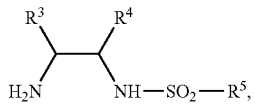

$R^3$ and $R^4$ are each independently C$_i$-C$_{20}$-alkyl, C$_4$-C$_{15}$-aryl or C$_5$-C$_{16}$-arylalkyl, or $R^3$ and $R^4$ together are a straight-chain or branched C$_3$-C$_{12}$-alkylene radical, and $R^5$ is C$_1$-C$_{20}$-alkyl, C$_1$-C$_{20}$-fluoroalkyl or C$_4$-C$_{15}$-aryl, and where, in the formula (IV):

arene and X are each as defined under formula (II) and (III) in the formula (IV) represents a compound of the formula (III) as defined there.

5. Process according to claim 4, wherein the ruthenium complex used is one obtainable by reacting a compound of the formula (II) with a compound of the formula (III).

6. Process according to claim 5, wherein the ruthenium complex used is one obtainable by reacting a compound of the formula (II) with a compound of the formula (III), wherein the molar ratio of the compound of the formula (III) to the compound of the formula (II) is 2:1 to 3:1.

7. Process according to claim 4, wherein the compound of the formula (II) is the (benzene)dichlororuthenium dimer, the (mesitylene)dichlororuthenium dimer or the (cumene)dichlororuthenium dimer.

8. Process according to claim 4, wherein the compound of the formula (III) is one wherein:

$R^3$ and $R^4$ are identical and are each phenyl or together are straight-chain C$_3$-C$_8$-alkylene, and $R^5$ is C$_i$-C$_4$-alkyl, C$_i$-C$_4$-fluoroalkyl, phenyl or naphthyl which is substituted by none, one, two, three, four or five radicals which are selected from the group consisting of C$_i$-C$_4$-alkyl, C$_i$-C$_4$-alkoxy, C$_i$-C$_4$-fluoroalkyl, fluorine and chlorine.

9. Process according to claim 4, wherein the compound of the formula (III) used is S,S- or R,R-N-p-toluenesulphonyl-1,2-diphenylethylenediamine.

10. Process according to claim 1, wherein the amine, at least some of which is present in protonated form, is one of the formula (V):

$$NR^6R^7R^8 \qquad (V)$$

where $R^6$, $R^7$ and $R^8$ are each independently hydrogen, C$_i$-C$_8$-alkyl or benzyl.

11. Process according to claim 10, wherein the amine, of which at least some is present in protonated form, is one of the formula (V) where $R^6$, $R^7$ and $R^8$ are each independently C$_i$-C$_8$-alkyl or benzyl.

12. Process according to claim 1, wherein a mixture of formic acid and triethylamine is used.

13. Process according to claim 1, wherein the molar ratio of formic acid to amine is 1:1 to 3:1.

14. Process according to claim 1, wherein the molar ratio of formic acid based on substrate used is 1:1 to 3:1.

15. Process according to claim 1, which is carried out at a reaction temperature of -10 to 150° C.

16. Process according to claim 1, which is carried out at a molar amount of ruthenium of 0.01 to 1.0 mol%, based on the substrate used.

17. Process according to claim 1, which further comprises stirring a reaction mixture at an average stirrer speed of 100 to 3 000 min$^{-1}$.

18. Process according to claim 1, which further comprises passing an inert gas stream through or over the reaction mixture.

* * * * *